United States Patent
Wick

(10) Patent No.: US 7,850,908 B1
(45) Date of Patent: Dec. 14, 2010

(54) DETECTING BACTERIA BY DIRECT COUNTING OF STRUCTURAL PROTEIN UNITS OR PILI BY IVDS AND MASS SPECTROMETRY

(75) Inventor: Charles H. Wick, Darlington, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 772 days.

(21) Appl. No.: 11/829,357

(22) Filed: Jul. 27, 2007

Related U.S. Application Data

(63) Continuation-in-part of application No. 10/314,328, filed on Dec. 9, 2002, now Pat. No. 7,250,138.

(51) Int. Cl.
*C12Q 1/68* (2006.01)
*G01N 15/06* (2006.01)
*G01N 33/00* (2006.01)
*G01N 33/48* (2006.01)
*G01N 9/30* (2006.01)

(52) U.S. Cl. .................. 422/50; 422/68.1; 422/82.01; 422/72; 422/81; 422/83; 436/43; 436/174; 436/178; 436/181; 73/1.01; 73/1.02; 73/1.03; 73/23.2

(58) Field of Classification Search .............. 422/50, 422/68.1, 82.01, 72, 81, 83; 436/43, 174, 436/177, 178, 181; 73/1.01, 1.02, 1.03, 23.2
See application file for complete search history.

(56) References Cited

U.S. PATENT DOCUMENTS

| | | | | |
|---|---|---|---|---|
| 4,113,434 A | * | 9/1978 | Tanaka et al. ............. 73/863.55 |
| 5,076,097 A | * | 12/1991 | Zarrin et al. ............... 73/61.72 |
| 5,090,257 A | * | 2/1992 | Bruce ....................... 73/863.03 |
| 5,164,604 A | * | 11/1992 | Blair et al. ................... 250/574 |
| 5,687,093 A | * | 11/1997 | Long et al. ..................... 703/1 |
| 5,711,916 A | * | 1/1998 | Riggs et al. .................... 422/83 |
| 5,760,314 A | * | 6/1998 | Bromberg et al. ......... 73/863.21 |
| 5,854,431 A | * | 12/1998 | Linker et al. ............. 73/863.23 |
| 5,904,752 A | * | 5/1999 | Willeke ........................ 95/216 |
| 6,051,189 A | * | 4/2000 | Wick et al. ............... 422/82.01 |
| 6,238,866 B1 | * | 5/2001 | Yeh et al. ........................ 435/6 |
| 6,485,686 B1 | * | 11/2002 | Wick ............................ 422/72 |
| 6,491,872 B1 | * | 12/2002 | Wick ............................ 422/72 |
| 6,584,865 B1 | * | 7/2003 | Doherty et al. .......... 73/863.03 |
| 6,777,228 B2 | * | 8/2004 | Lejeune ................... 435/309.1 |
| 7,250,138 B2 | * | 7/2007 | Wick ............................ 422/50 |

* cited by examiner

*Primary Examiner*—Brian J Sines
(74) *Attorney, Agent, or Firm*—Ulysses John Biffoni

(57) ABSTRACT

A system and method for detecting the presence of submicron sized particles in a sample taken from the environment. More particularly, the system may be used to detect and identify bacteria by detecting the presence of bacterial pili which have been separated from bacterial cells in the sample. The system includes means for collecting a sample from the environment, separating pili from bacteria in the sample, and purifying and concentrating the submicron sized pili in the sample based on the size of the pili. The purified and concentrated pili are detected with an apparatus which includes an electrospray assembly having an electrospray capillary, a differential mobility analyzer which receives output from the capillary, and a condensation particle counting device for counting the number of pili sized particles that pass through the differential mobility analyzer.

16 Claims, 17 Drawing Sheets

Cartridges Composed of Bundles of Membranes
Wide Range of Pore Sizes

Cartridges Composed of Bundles of Membranes
Wide Range of Pore Sizes

DETECTING BACTERIA BY DIRECT COUNTING OF STRUCTURAL PROTEIN UNITS OR PILI BY IVDS AND MASS SPECTROMETRY

RELATED APPLICATIONS

This application is a Continuation-In-Part of U.S. patent application Ser. No. 10/314,328 filed on Dec. 9, 2002, issued as U.S. Pat. No. 7,250,138 on Jul. 31, 2007, which is incorporated herein by reference.

GOVERNMENT INTEREST

The invention described herein may be manufactured, licensed, and used by or for the United States Government. The invention also relates to U.S. Pat. Nos. 6,051,189, 6,485,686, 6,491,872, and 7,250,138 all assigned to the United States Government and incorporated by reference herein.

BACKGROUND OF THE INVENTION

1. Field of the Invention

The present invention relates to the detection, identification and monitoring of submicron size particles. More particularly, the invention pertains to apparatus and methods for the sampling, measuring, characterizing, automated detection, identification, and monitoring of submicron size particles. Preferably, the present invention provides for the sampling, detection and identification of submicron size particles having a size range of from about 5 to about 1000 nanometers. Such particles include viruses and virus-like agents (such as, for example, prions, viral subunits, viral cores of delipidated viruses, plant viruses, etc.), and other biological materials such as nanometer size portions of bacteria.

2. Fields of Use of the Invention

Detection and identification of viruses without limiting the detection and identification to a particular family, genus and species and searching for viruses pathogenic to humans in a single environment can be difficult.

As set forth in U.S. Pat. Nos. 6,051,189, 6,485,686, 6,491,872, and 7,250,138, assigned to the U.S. Government and herein incorporated by reference, viruses may also be extracted from an environment and concentrated to an extent that permits detection and monitoring of viruses, without culturing procedures. Generally, in the detection of small amounts of viruses in environmental or biological liquids, it may be necessary to both enrich the concentration of viruses many orders of magnitude (i.e., greatly reduce the volume of liquid containing the viruses) and accomplish removal of non-viral impurities. In the presence of non-viral impurities, even the most sensitive detection methods generally require virus concentrations on the order of 10 femtomoles/microliter or more in the sampled liquid to reliably detect the viruses.

Sampling for airborne viruses is generally accomplished by collecting airborne particles in liquid, using a process such as air scrubbing, or eluting from filter paper collectors into a liquid medium. Collection and subsequent separation and detection methods are affected by the adsorption of viruses into solids in aerosols and liquids.

In contrast, when sampling liquids for viruses, in many cases no special equipment or processes may be necessary in order to collect a sample; for example, in sampling blood and other body fluids for viruses, only a standard clinical hypodermic needle may be needed. For sampling of bodies of water or other conveniently accessible liquids, sample collection may not be an issue at all, and in such cases the term "collector" is often applied to what is, in reality, a virus extraction step (such as collection on a filter).

Bacteria are different types of microorganisms than viruses. Viruses are a magnitude smaller in size than bacteria. Bacteria are classified in their own scheme. They have cell walls or are organized into cellular components and generally are considered to be among the self-sustaining organisms. Viruses require a living cell to invade in their life cycle. The technology and processes disclosed in U.S. Pat. Nos. 6,051,189, 6,485,686, 6,491,872, and 7,250,138 capitalize on the size and physical properties of the viruses to separate, count and characterize them. There is sufficient information from this characterization to identify them and perform investigative studies.

Bacteria are generally 0.5-1 microns wide and 2-3 microns long, and generally outside the physical ability of the apparatus disclosed in the referenced U.S. Pat. Nos. 6,051,189, 6,485,686, and 6,491,872. Bacteria have, however, interesting features that are in the proper size range for the apparatus to characterize. For example, gram-negative bacteria, named because of their inability to retain crystal violet-iodine complex stain, have rigid surface appendages called "pili." These "hair-like" structures are around 7 nm in diameter and vary in length, up to 25 nm for the longer flagellae, which are other nanometer-sized structures that can be attached to the surface of bacteria. The pili are composed of structural protein subunits called "pilins." Some structures have only one structural protein unit, other pili are more complex and have several. These pili consist of a precise helical arrangement of one or more types of protein and as indicated may have different lengths for different bacteria. Choudhury, et. al (1999): Science 7 Aug. 99 285:1061 and David Eisenberg: How chaperones protect virgin proteins (Science 13 Aug. 99 285:1021), discuss crystal complexes associated with pilin subunits. Cell lysis breaks the cell into components. Lysis can be achieved by changes in pH, temperature, sonic treatment or by chemical means.

Processes for the separation and collection of pili from bacteria are generally set forth in U.S. Pat. Nos. 4,443,431 (Buchanan et. al.), 4,472,302 (Karkhanis), 4,702,911 (McMichael), 4,740,585 (Schmidt et. al.), 4,971,794 (Linggood et. al.), 5,612,036 (Hodges et. al.), 5,750,116 (Brinton), 5,968,769 (Green et. al.), and 6,291,649 (Lindberg et. al.), the teachings of which are fully incorporated herein by reference. Generally, heat, chemical activity and physical means can be used to release the pili from the bacteria. The pili can then be separated from the bacteria cells and counted as nanometer sized particles. Further, it is expected that different pili proteins for different bacteria species can be expected to be separated and identified. Identification of pili as nanometer sized particles and rapid identification and classification of the bacteria according to the nanometer sized characteristics of the pili is desired.

SUMMARY OF THE INVENTION

The present invention relates to a method and apparatus for rapidly detecting and identifying the presence of different bacteria in an environment. A collecting means is utilized to collect liquid and gaseous samples from the environment. In some cases, a means for purifying and/or concentrating the bacteria, such as a filtering means, may be necessary to remove extraneous substances and impurities from the bacteria in the collected sample.

A separating means is then used to remove the pili from the bacteria. This may be accomplished by the application of one or more of heat, chemicals and/or mechanical or physical energy. The system then includes a means for purifying and/or concentrating the separated pili. The system also includes a means for detecting the purified and concentrated or separated pili, wherein the detecting means comprises: an electrospray assembly, the assembly having an electrospray capillary which receives the output from the purifying and concentrating means, a differential mobility analyzer which receives the output from the capillary, and a condensation particle device for counting the number of particles that pass through the differential mobility analyzer. Automated control means can be utilized to control the flow of sample through the system. A biomarker means or other calibrating means may be mixed with the sample and utilized to correlate the results with the known size or concentration of the biomarker or calibrating means.

In a more general sense, the method for detecting the presence of submicron sized particles in a sample taken from the environment, includes the steps of collecting a sample from the environment, purifying and concentrating the submicron size particles in the sample based on size; and detecting the purified and concentrated particles with a detecting means comprising an electrospray assembly which has an electrospray capillary which receives the output from the purifying and concentrating means, a differential mobility analyzer which receives the output from the capillary, and a condensation particle device for counting the number of particles that pass through the differential mobility analyzer.

The bacteria can be identified by detecting the different pili that can be removed from the bacteria. A separating means may include one or more of a chemical means, heating means, or physical means or mechanical means to remove the pili from the bacteria. Purifying means can be used to separate the submicron or virus-size pili from the larger material, such as bacteria. The separated pili can then be detected and categorized according to their physical characteristics, such as the size of the pili. A means for detecting the purified and concentrated pili includes an electrospray assembly, the assembly having an electrospray capillary which receives the output from the purifying or concentrating means, a differential mobility analyzer which receives the output from the capillary, and a condensation particle device for counting the number of particles that pass through the differential mobility analyzer. A biomarker means or other calibrating means may be mixed with the sample and utilized to correlate the results with the known size or concentration of the biomarker or calibrating means.

In more general terms, a system and method for detecting the presence of submicron sized particles having a size range of from about 5 to about 1000 nanometers in a sample taken from the environment is provided herein. The system includes a collecting means for collecting a sample from the environment and a means for purifying and concentrating or separating the submicron particles in a sample by purifying and concentrating or separating the particles based on size. The purifying and concentrating or separating means includes a means for connecting the collecting means to the purifying and concentrating means for transferring the sample from the collecting means to the means for purifying and concentrating the particles. The system also includes a means for detecting the purified and concentrated or separated particles, wherein the detecting means comprises: an electrospray assembly, the assembly having an electrospray capillary which receives the output from the purifying and concentrating means, a differential mobility analyzer which receives the output from the capillary, and a condensation particle device for counting the number of particles that pass through the differential mobility analyzer. A biomarker means or other calibrating means may be mixed with the sample and utilized to correlate the results with the known size or concentration of the biomarker or calibrating means. In a more specific application, the device can include a means for separating pili from bacteria collected from a sample, and the pili can then be processed and detected as is done for other submicron sized particles.

The collecting means may comprise an ultracentrifuge for density-gradient ultracentrifugation so that the particles are banded according to density, or a collector having means for liquid scrubbing a collected fluid sample of aerosol and gaseous materials containing the particles and a means for reducing the size of solid materials in the fluid sample. The collecting means may also comprise a liquid sample collector. The collecting means is intended to collect a sample containing submicron size particles having a size from about 5 to about 1000 nanometers and are selected from the group consisting of viruses, prions, macromolecules, proteins and satellites, viral subunits, viral cores of delipidated viruses, and plant viruses. Further examples include standard particles used for calibrating equipment, coated particles, spherical particles, metallic-core shelled particles, polymers, fluorescent microspheres, powders, nanoclusters, particles produced as a result of manufacturing processes, and other chemical and biological materials such as nanometer size portions of bacteria such as pili.

The system also includes a means for detecting the purified and concentrated particles such as bacterial pili, wherein the detecting means comprises: an electrospray assembly, the assembly having an electrospray capillary which receives the output from the purifying and concentrating means; a differential mobility analyzer which receives the output from said capillary; and which receives the output from the capillary, and a condensation particle device for counting the number of particles that pass through the differential mobility analyzer. Automated control means can be utilized to control the flow of sample through the system.

The method for detecting the presence of submicron sized particles or pili in a sample taken from the environment, includes the steps of collecting a sample from the environment, purifying and concentrating the submicron size particles in the sample based on size; and detecting the purified and concentrated particles with a detecting means comprising an electrospray assembly which has an electrospray capillary which receives the output from the purifying and concentrating means, a differential mobility analyzer which receives the output from the capillary, and a condensation particle device for counting the number of particles that pass through the differential mobility analyzer.

Accordingly, an object of the present invention is to detect known and unknown or submicron size particles.

Another object of the present invention is to provide a method and apparatus for the efficient and rapid detection and identification of bacteria based on the physical characteristics of pili particles separated from the bacteria.

A further object of the present invention to provide an automated system for the detection and identification of bacteria based on the characterization of the submicron size pili particles.

These, together with still other objects of the invention, along with the various features which characterize the invention, are pointed out with particularity in the appended claims.

BRIEF DESCRIPTION OF THE DRAWINGS

Other objects and advantages of the invention will become apparent upon reading the following detailed description with reference to the attached drawings, wherein.

DETAILED DESCRIPTION OF THE INVENTION

Figure 1:
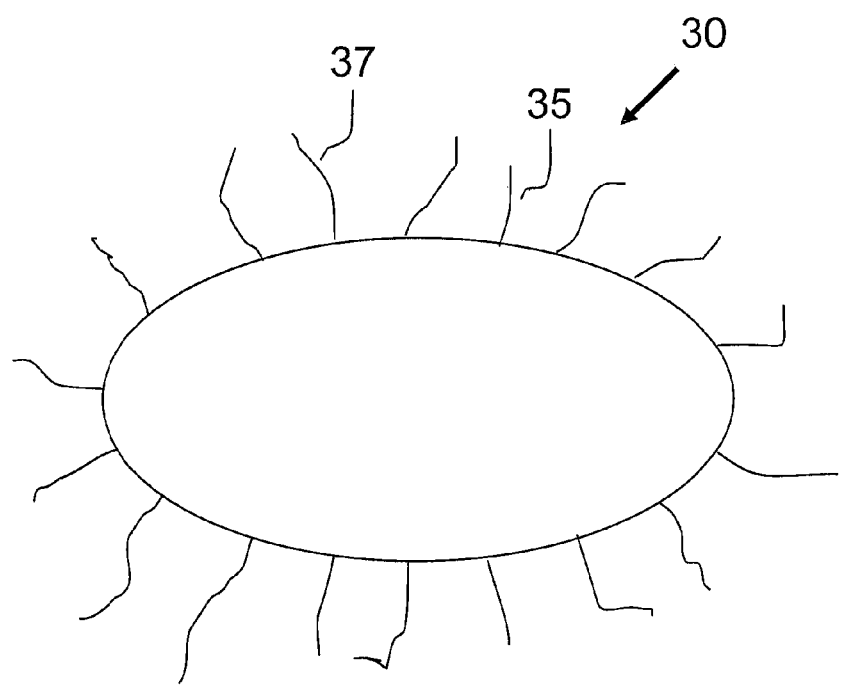
FIG. 1 is a representation of a bacterial cell having one or more pili.

Referring to FIG. 1, there is shown generally a representation of a bacterial cell 30 having one or more pili attached to the outer surface of the bacterial cell. Bacteria may have more than one type of pili as generally represented by numbers 35 and 37. Pili are present on a variety of different types of bacteria as generally represented in Table 1, below.

TABLE 1

Some properties of pili and fimbriae.

| Bacterial species where observed | Number on cell | Distribution on cell surface | Function/Comment |
|---|---|---|---|
| *Escherichia coli* (F or sex pilus) | 1-4 | uniform | mediates DNA transfer during conjugation |
| *Escherichia coli* (common pili or Type 1 fimbriae) | 100-200 | uniform | surface adherence to epithelial cells of the GI tract/Type 1 |
| *Neisseria gonorrhoeae* | 100-200 | uniform | surface adherence to epithelial cells of the urogenital tract/Type 4 |
| *Neisseria gonorrhoeae* | 100-200 | uniform | promote bacterial aggregation, microcolony formation/Type 4 |
| *Streptococcus pyogenes* (fimbriae plus the M-protein) | ? | uniform | adherence, resistance to phagocytosis; antigenic variability |
| *Pseudomonas aeruginosa* | 10-20 | polar | surface adherence/Type 4 |
| *Sulfolobus acidocaldarius* | ? | ? | attachment to sulfur particles |
| *Haemophilus influenzae* | | uniform | adhesion and colonization of the upper respiratory mucosa |
| *Vibrio cholerae* | | Type 4 | |
| *Mycobacterium bovis* | | | |
| *Neisseria meningitidis* | | Type 4 | |
| *Salmonella enterica* serovar | | Type 4 | |
| *Myxococcus xanthus* | | Type 4 | |
| *Moraxella lacunata* | | Type 4 | |
| *Moraxella nonliquifaciens* | | Type 4 | |
| *Dichelobacter nodosus* | | Type 4 | |
| *Eikenella corrodens* | | Type 4 | |
| *Citrobacter rodentium* | | Type 4 | |
| *Synechocystis* sp. | | | |
| *Moraxella bovis* | | | |
| *Bordetella pertussis* | | | Respiratory epithelium |

| Types of Pili | | | |
|---|---|---|---|
| Type | Size | Function | Comment |
| P Pili | 1000-2000 nm long | Binds to uroepithelial cells | Thick, rigid filaments |

TABLE 1-continued

| | | | |
|---|---|---|---|
| Type 1 Pili | | Binds to urinary bladder epithelium | |
| Type 4 Pili | ~6 nm wide by ~4000 nm long | Twitching motility | Flexible; often polar |
| Curli Pili | ~4 nm wide | Mediate binding to a variety of host proteins | Thin, irregular, highly aggregated flexible filaments |
| CSA or CFA type Pili similar to Type 1 pili | | Morphologically | |

Figure 2:
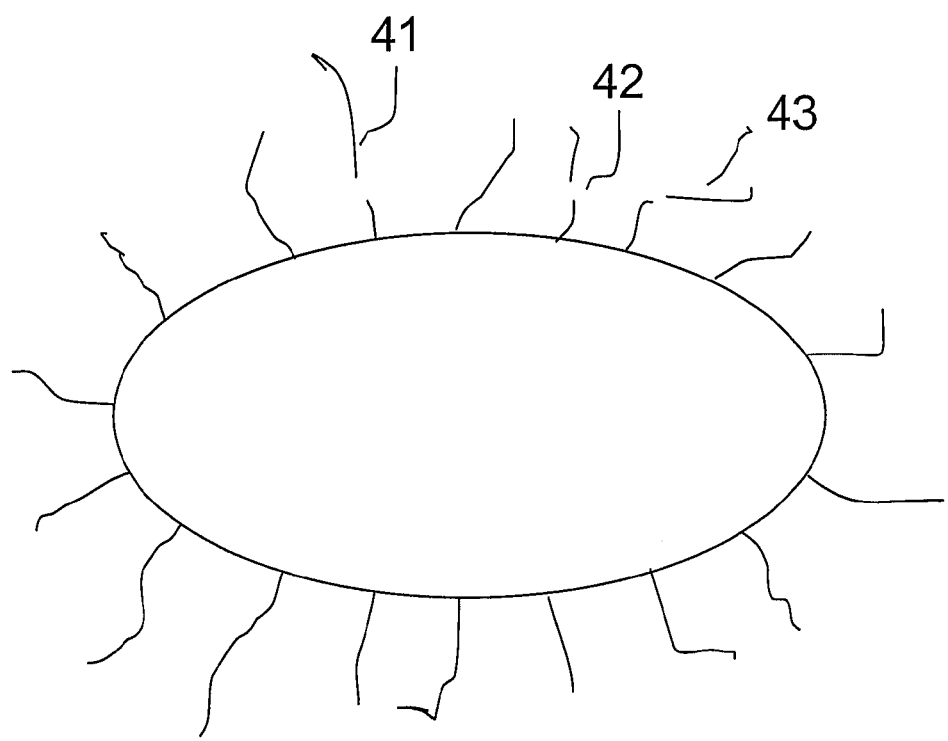
FIG. 2 is a representation of pili after being removed from a bacteria surface.

FIG. 2 is an illustration of pili after being removed from the surface of a bacteria cell. The pili when removed from the surface of the bacteria cell may have fragments of different lengths 41, 41 and 43. Some fragments of the pili may remain attached to the surface of the bacterial cell.

Figure 3:
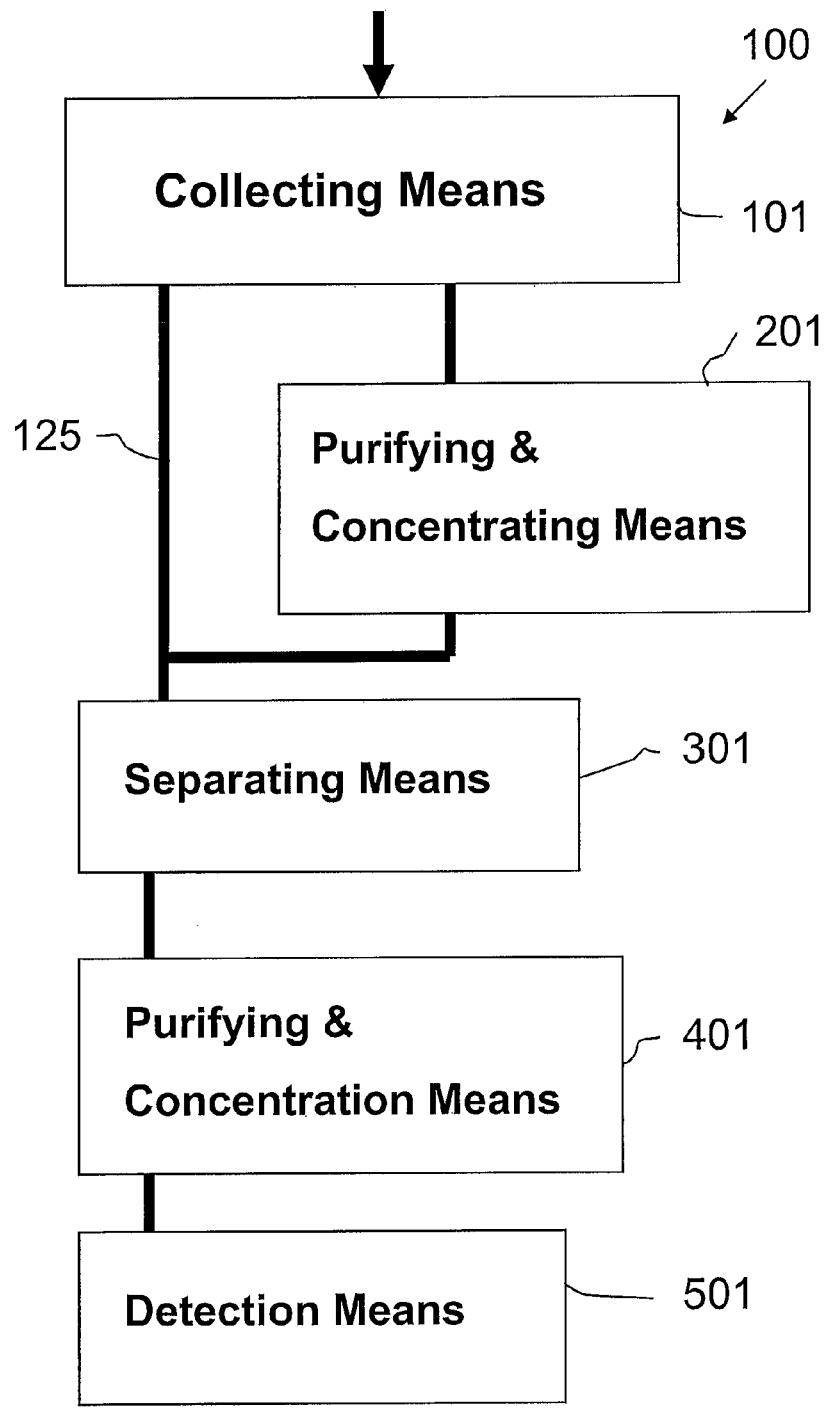
FIG. 3 is a block diagram generally depicting a system and method for detecting bacteria.
Figure 4:
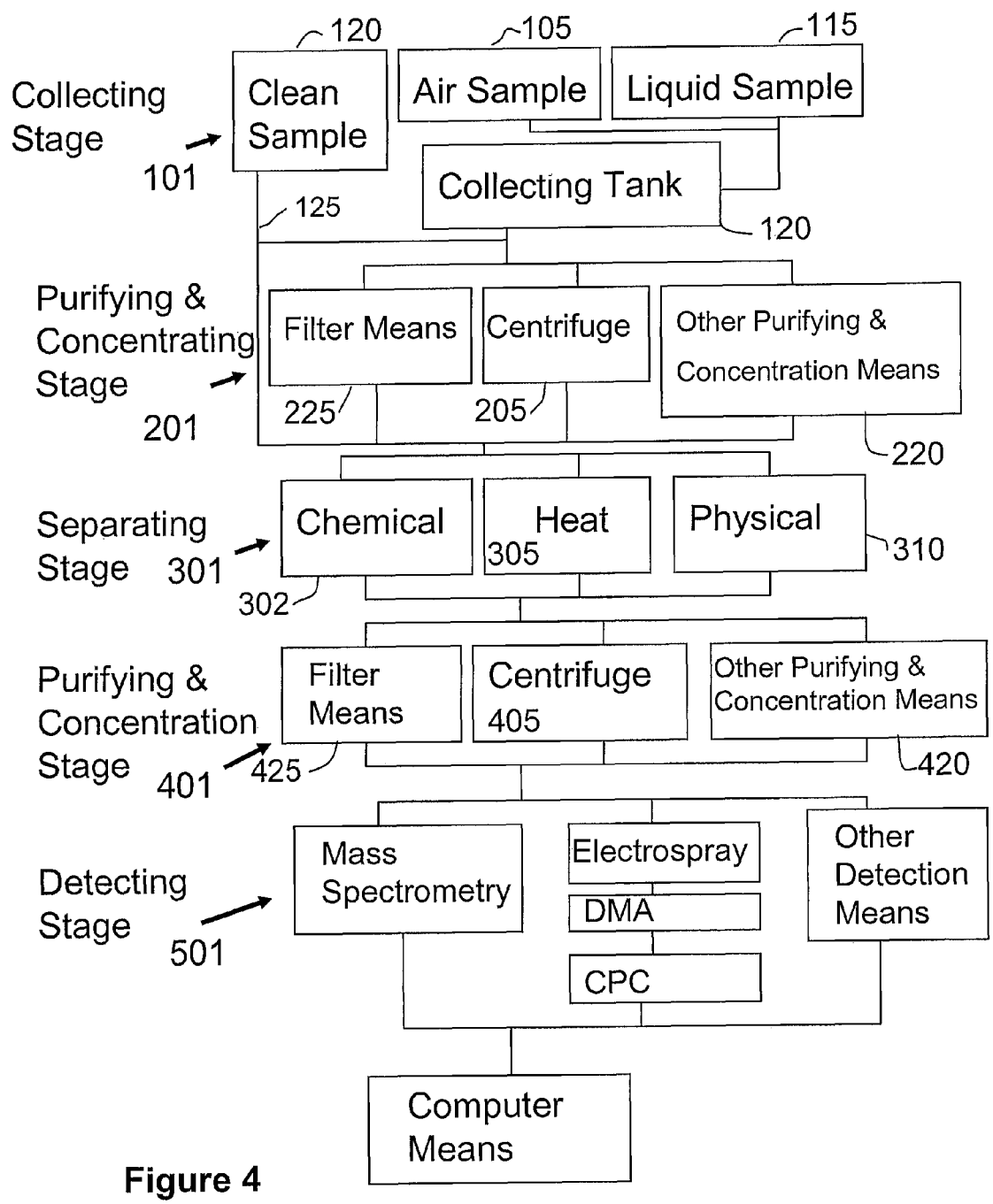
FIG. 4 is a more detailed schematic diagram of FIG. 3.

FIG. 3 is a block diagram generally depicting a system 100 and method for detecting the presence of bacteria. This is accomplished by detecting the presence of bacterial submicron sized pili particles having a size range of from about 5 to about 1000 nanometers in a sample taken from the environment. The system includes a collecting stage or means 101 for collecting a sample from the environment. As shown in FIG. 4, the collecting means 101 may have a liquid scrubbing means 105 for collecting samples of aerosol and gaseous samples from the environment. For liquid samples, a liquid collecting means 115 may also have a means for reducing the size of solid materials in the fluid sample. In those instances where the sample is removed from surfaces such as floors and walls with some type of wipe, the wiping material is normally soaked in fluid to place the sample in solution. The collected air, aerosol and liquid samples may be further processed in a collecting tank 120 to break up clumps of sample materials. In those instances in which a clean or relatively pure bacterial sample 125 is being processed, the sample may be fed directly to the purifying and concentrating stage 201.

As shown in FIGS. 3 and 4, a first purifying and concentrating stage or means 201 includes a means for purifying and concentrating the bacteria in the sample from other materials based on the size of the bacteria in relation to other smaller and larger particles. The smaller particles have a size range of from about 5 to about 1000 nanometers and examples of such submicron size particles include viruses, prions, macromolecules, proteins and satellites, viral subunits, viral cores of delipidated viruses, and plant viruses. It would be helpful to remove these submicron size particles from the sample before the pili are separated from the bacteria since pili have size ranges of from within a range from 5 to about 1000 nanometers. This separation may be accomplished, for example, by use of an ultracentrifuge 205 for density-gradient ultracentifugation so that the sample particles are banded according to density. Further, a filter means 225 or other purifying and separation means 220 may be used for removing both particles smaller and larger than a predetermined size range of bacteria expected to be present in the sample. Along with the separation of particles of a particular size range from the sample this process also may serve to concentrate the bacteria in the sample.

Figure 5:
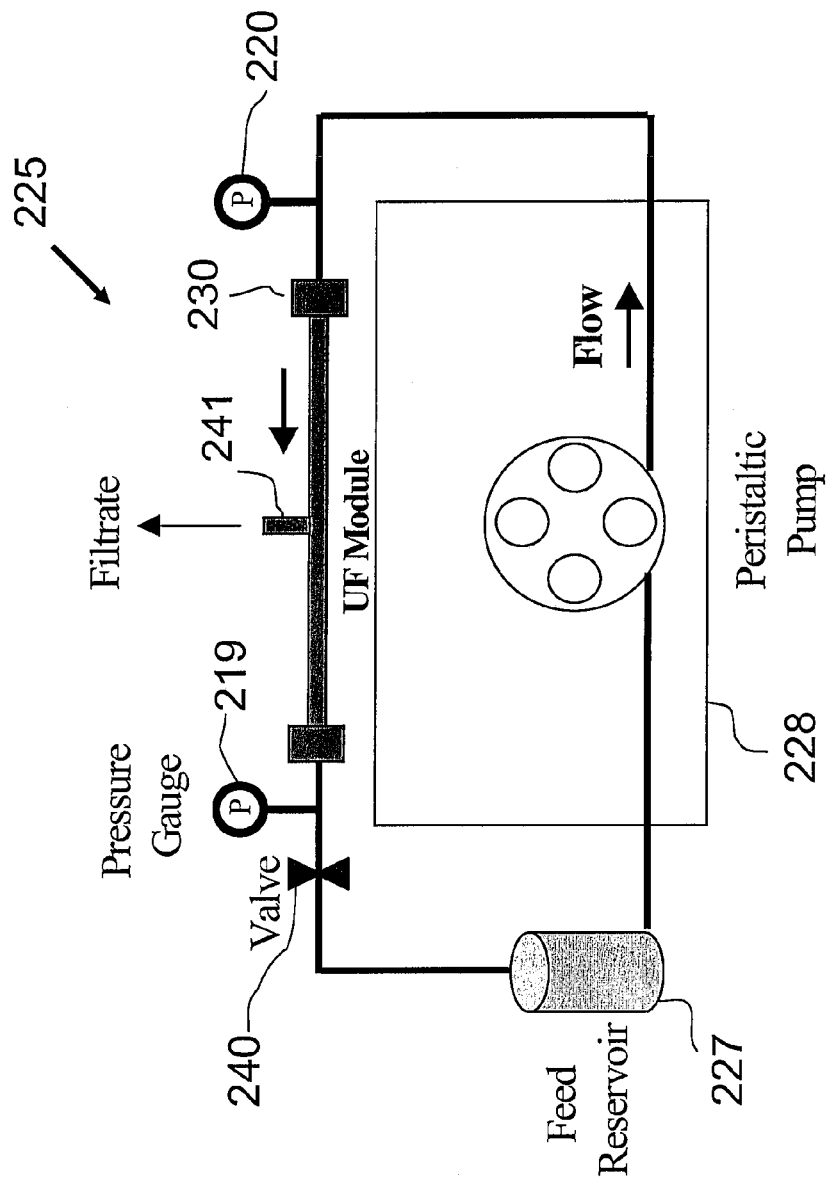
FIG. 5 is a representation of a first filtration means of FIG. 4.
Figure 6:
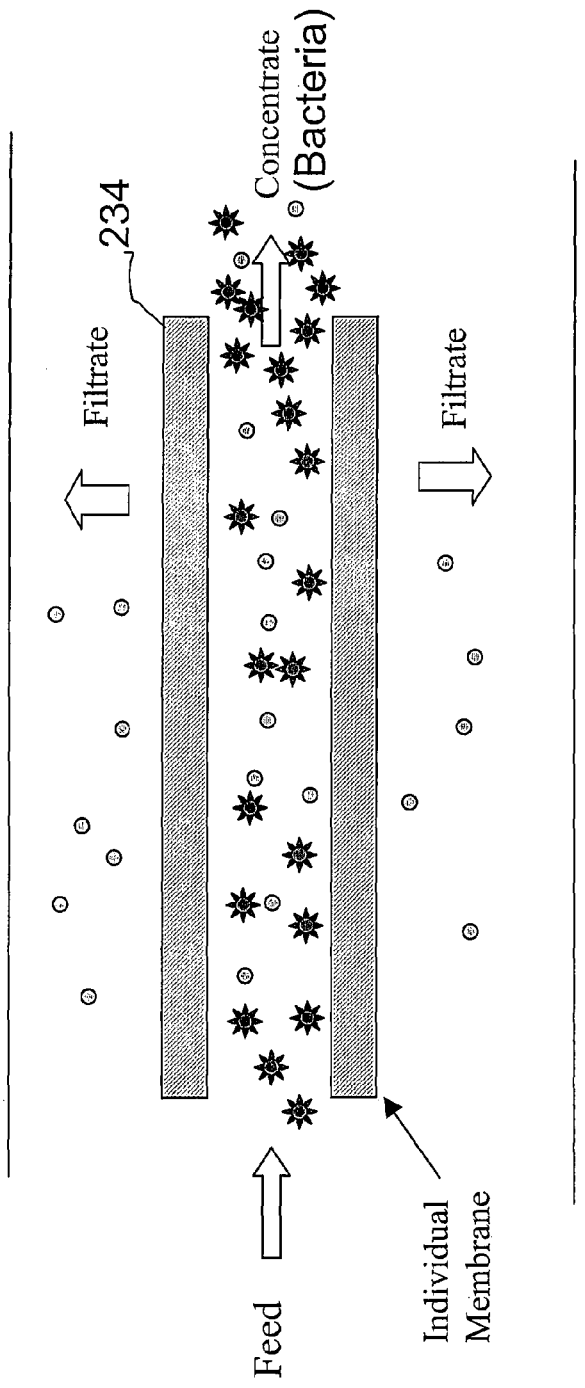
FIG. 6 is a cross-sectional representation of a filter element of FIG. 5.
Figure 7:
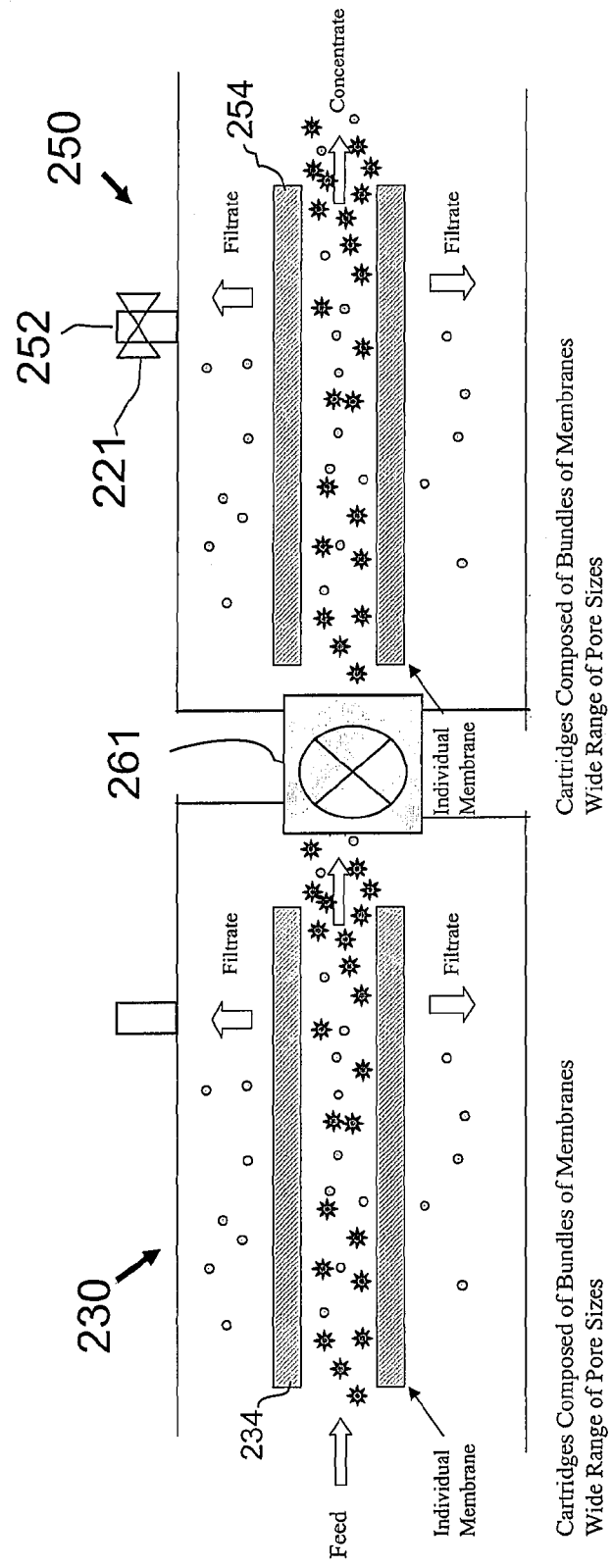
FIG. 7 is a representation of another filtration module of the type in FIG. 5.

FIGS. 5, 6 and 7 show further details of one embodiment of a filter means 225 with filter containers 230 and 250. With the filter means 225, a sample is first placed in the feed reservoir 227 and then a peristaltic pump 228 is turned on to cause the sample to flow through the filter container 230. As the sample is fed through a tubular or first cross-flow filter 234 housed within the filter container, the filtrate, which may include salts and proteins, which are smaller than bacteria cells, are forced through the filter 234 leaving the bacteria in the sample contained within the filter. The sequential filter container 250 may have a cross flow filter 254 which has pore sizes larger than bacteria so that the filtrate 254 contains the bacteria sample, thus removing particles both smaller and larger than the bacteria sample. Sequential arrangements of different pore size ultrafilters can be picked to selectively control the flow of a particle with a chosen size range so that the chosen particles to thereby purify and concentrate a fluid sample limited to particles within the chosen size range. Control valve 221 and pressure indicators 219 and 220 are used to regulate the flow rate and pressures within the filter container 250.

FIG. 7 shows another embodiment of a filter means 225 with sequential filter containers 230 and 250. With the filter means 225, a sample is first placed in the feed reservoir 227 and then a peristaltic pump 228 is turned on to cause the sample to flow through the filter container 230. As the sample is fed through a tubular or first cross-flow filter 234 housed within the filter container, the filtrate, which may include salts and proteins, which are smaller than bacteria cells, are forced through the filter 234 and are removed from the filter container 230 as filtrate, leaving the bacteria in the sample contained within the filter (the concentrate). The sequential filter container 250 may have a cross flow filter 254 which has pore sizes larger than bacteria so that the filtrate 252 contains the bacteria sample, thus removing particles both smaller and larger than the bacteria sample. Sequential arrangements of different pore size ultrafilters 234 and 254, and valves 240 and 221 can be chosen to selectively control the flow of a particle with a chosen size range so that the chosen particles to thereby purify and concentrate a fluid sample limited to particles within the chosen size range In the purifying and concentrating stage 201, another means for purifying and concentrating the bacteria sample comprises a centrifuge 205 of the type disclosed in U.S. Pat. Nos. 6,051,189, 6,485,686, 6,491,872, and 7,250,138. After centrifugation, the gradient imprisoned in the rotor of the centrifuge 205 can be divided into two parts: the useful part which contains that range (or in some cases, those ranges) of densities in which the particles to be detected are expected to lie, and the remainder which will generally be discarded and not sent on to the next stage. Thus, for example, in the detection of viruses pathogenic to humans, this useful part could be that part of the gradient corresponding to densities of 1.175-1.46 g/ml; alternatively, a subset of this range could constitute the useful range if only certain viruses are being analyzed. Similarly, in the centrifuging of samples containing bacteria, there may be a range of bacteria densities that are desired to be separated out from the centrifuge gradient. Further, since the pili will be separated from the bacteria in the subsequent separating stage 301, it is expected that particles smaller than 1000 nanometers would be separated out as non-useful parts of the gradient and disposed of as waste.

The useful part of the gradient containing the bacteria will then be passed on to the separating stage 301. One advantage of the ultracentrifuge is that for large sample volumes with small quantities of bacteria, for example monitoring of bodies of water, such as drinking water sources, a continuous-flow density gradient ultracentrifugation could be used for continuous testing. In continuous flow operation, the bacteria-containing liquid stream is pumped in from the collection stage 101 and flows continuously over the density gradient in the rotor of the centrifuge 205, and bacteria sediment out of the stream, banding into the density gradient according to buoyant density. This pumping of sample into and out of the centrifuge 205 can be performed with the centrifuge spinning at high speed. Alternatively, for fixed sample volumes, with ordinary zonal operation (not continuous-flow), the sample does not flow continuously into the centrifuge 205 for long periods of loading, but rather the entire sample volume, which must be less than the annular volume of the centrifuge, is loaded into the centrifuge. The rotor volume is then closed off before acceleration to high speed. After loading and centrifuging to achieve banding, the bacteria-containing bands are recovered by displacing the bands sequentially, with lowest density bands exiting first and highest density last. As the density of each bacteria uniquely determines the position of that virus or particle in the exiting stream, the timing of the detection of specific bacteria particles provides particle density information.

In operation, sample liquid is introduced into the density gradient within the centrifuge 205 rotor at the low-density end of the gradient, and each particle or molecule penetrates into the gradient at a rate that increases with the mass of the particle, and with the density. In the case of a protein molecule, the mass is much smaller than that of a virus by at least an order of magnitude, and the density is about the same as that of a relatively low-density virus. Accordingly, the rate of banding for proteins is much slower than for viruses. The proteins will then primarily be to the low-density side of their equilibrium positions, as they started on that side. Since the equilibrium position of most proteins in a gradient is nominally about 1.3 g/ml, at the operating time, most proteins are positioned considerably lower than 1.3. Once the bacteria are banded, the centrifuge is decelerated to low speed, and the gradient is recovered by pumping dense fluid of preferably 60% CsCl from the gradient supply system to the centrifuge. The dense fluid displaces the gradient, with low density bands exiting first followed by high density bands. The procedure is complete in a few minutes, and the cycle repeats again beginning with the loading of the density gradient at low speed. Ultracentrifugation provides the advantages of universal capture of all catalogued and non-cataloged bacteria, with high capture efficiencies and a high degree of bacteria separation from the background components.

Figure 8:
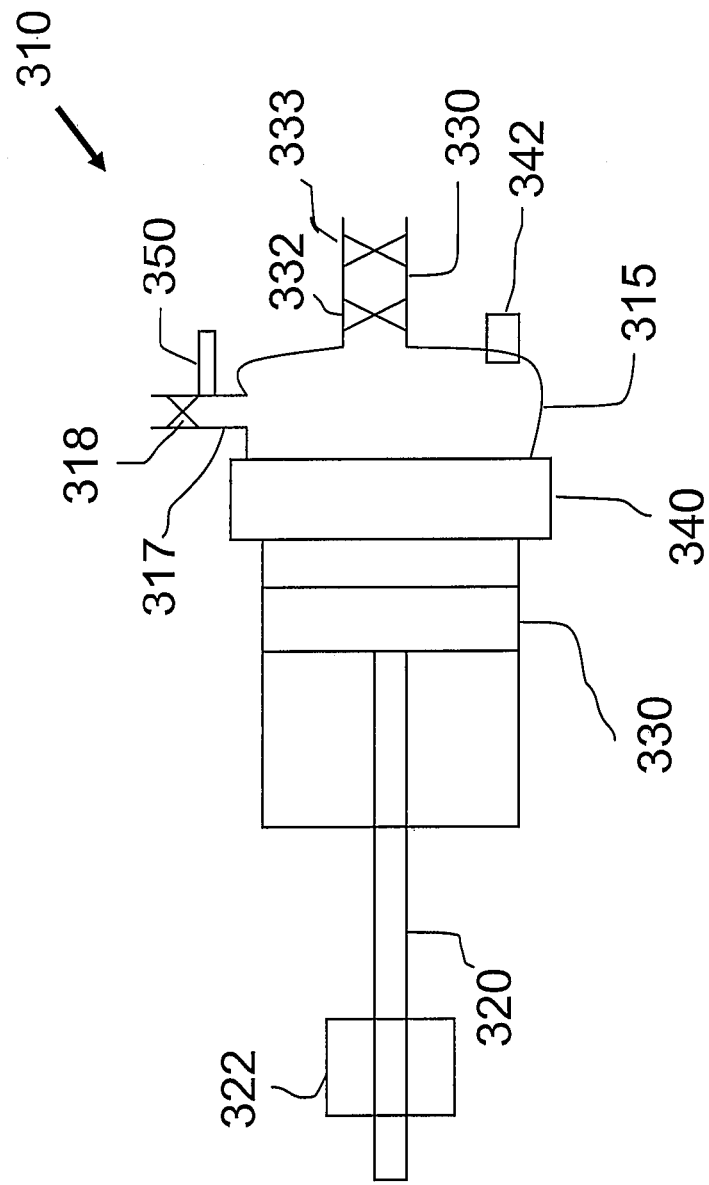
FIG. 8 is a representation of a physical or mechanical separating means of FIG. 4.

After passing through the purifying and concentrating stage 201 the sample containing the bacteria is then fed to the separating stage 301 for separating the pili from the surfaces of the bacteria. This may be done by chemical means 302, heat 305, mechanical or physical means 310, or combinations thereof. In the embodiment shown in FIG. 8, the separation stage 301 comprises a mechanical separating means 310 for mechanically removing the pili from the surface of the bacteria includes a housing or chamber 315, an inlet conduit 317 having a valve means 318, a plunger 320, a motor 322 for selectively moving the plunger in the chamber, and an outlet 330. The outlet may include an adjustable restriction 332 and an outlet valve 333. The liquid sample from the purifying and concentrating stage 201 enters the chamber 315 through inlet 317 having a valve 318 for controlling the flow of liquid into the chamber. As liquid enters the chamber 315 the plunger 320 is withdrawn in a careful manner by the motor 322. When the chamber 315 is substantially filled, a slight forward movement of the plunger 320 causes any residual air to be removed from the chamber 315 and the valve 318 is closed. After outlet valve 333 is opened, separation of the pili from the surface of the bacteria may be produced by using the plunger 320 to force the liquid sample out of the chamber 315 through the outlet 330 having an adjustable restriction 332. For testing consistency, the volume of liquid sample should be about the same for the different pili separations. Also the movement rate of the plunger and size of the restriction should be selectively controlled for different separations. Additional control for the pili separation process may include a circumferential heater 340 for applying a controlled amount of heat to the chamber 315 and the liquid sample. A thermometer 342 is connected to the chamber 315 for measuring the heat or temperature applied to the sample. Further, chemicals such as sodium hydroxide, ammonium acetate, and others well known in the art, can be used to adjust the pH and disrupt the cell wall of the bacteria to produce separation of the pili from the bacteria. These chemicals may be introduced into the chamber through a small valve controlled tube or capillary 350.

Figure 9:
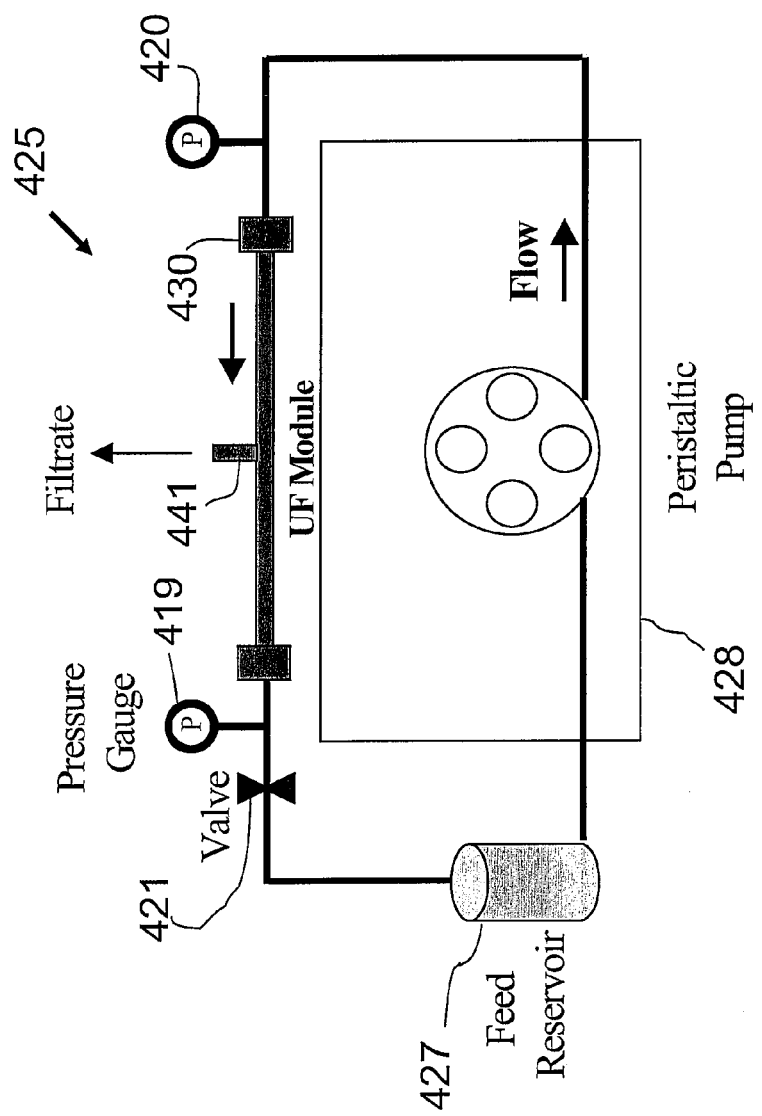
FIG. 9 is a representation of a second filtration means of FIG. 4.
Figure 10:
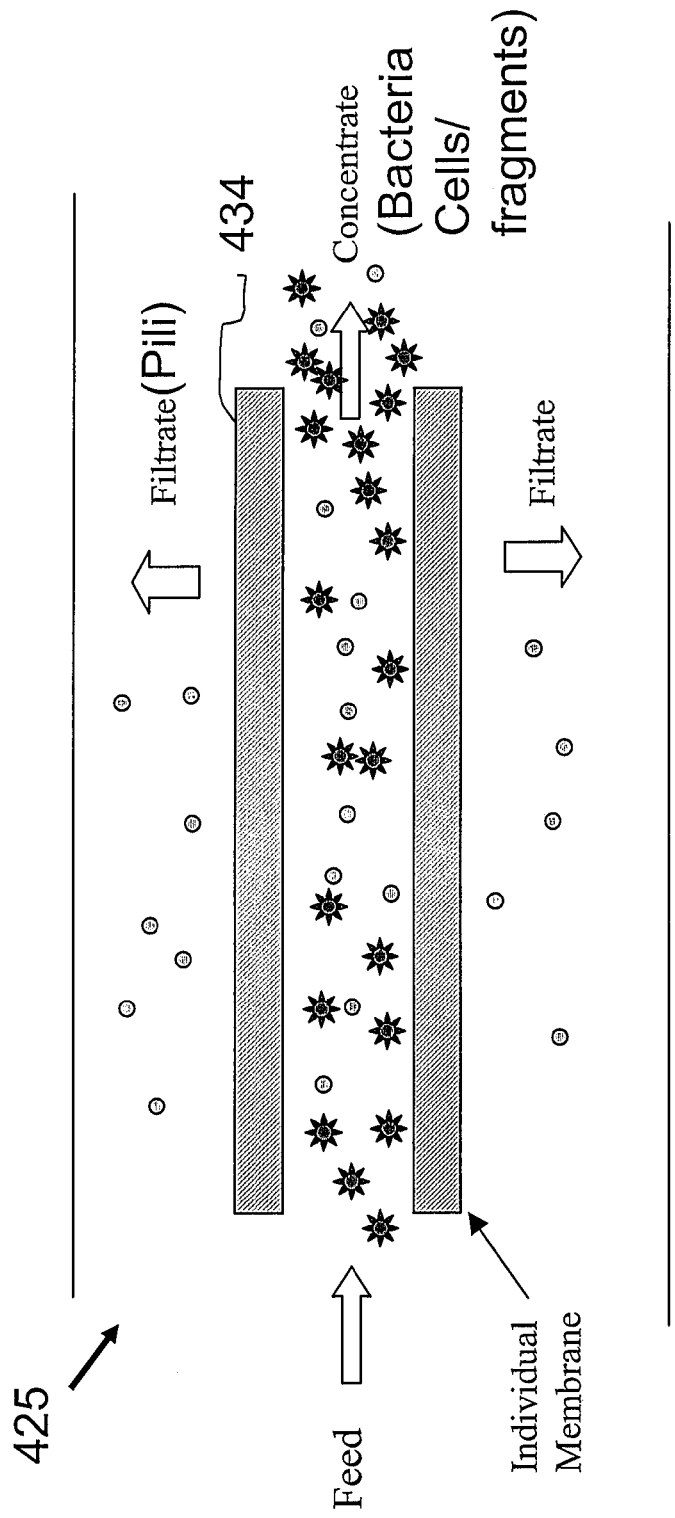
FIG. 10 is a representation of a filter element of FIG. 9.

After the pili have been removed or separated from the bacteria, the solution passes to a second purifying and concentrating stage 401 where the pili are separated from the bacteria cells. FIGS. 9 and 10 show further details of a filter means 425 with filter container 430, which comprise one embodiment for purifying and/or concentrating the pili. With the filter means 425, a sample is first placed in the feed reservoir 427 and then a peristaltic pump 428 is turned on to cause the sample to flow through the filter container 430. As the sample is fed through a tubular or cross-flow filter 434 housed within the filter container, the filtrate, which includes pili, which are smaller than bacteria cells, are forced through the filter 434 and removed from the filter container as filtrate, leaving the pili-stripped bacteria cells contained within the filter 434. Control valve 421 and pressure indicators 419 and 420 are used to regulate the flow rate and pressures within the filter container 430.

In the purifying and concentrating stage 401, another means for purifying and concentrating the pili separated from the bacteria sample in the separating stage 301, comprises a centrifuge 405 of the type disclosed in U.S. Pat. Nos. 6,051,189 and 6,485,686. After centrifugation, the gradient imprisoned in the rotor of the centrifuge 205 can be divided into two parts: the useful part which contains that range (or in some cases, those ranges) of densities in which the particles to be detected are expected to lie, and the remainder which will generally be discarded and not sent on to the next stage. Thus, for example, in the detection of viruses pathogenic to humans, this useful part could be that part of the gradient corresponding to densities of 1.175-1.46 g/ml; alternatively, a subset of this range could constitute the useful range if only certain viruses are being analyzed for. Similarly, in the centrifuging of samples containing pili, there may be a range of pili densities that are desired to be separated out from the centrifuge gradient. Further, it is expected that pili particles smaller than 1000 nanometers would be separated out as the useful parts of the gradient and passed on to the detecting stage 501.

One advantage of the ultracentrifuge is that for large sample volumes with small quantities of pili, for example in monitoring of bodies of water, such as drinking water sources, a continuous-flow density gradient ultracentrifugation could be used for continuous testing. In continuous flow operation, the pili-containing liquid stream from the separating stage 301 flows continuously over the density gradient in the rotor of the centrifuge 405 and are banded into the density gradient according to buoyant density. This pumping of sample into and out of the centrifuge 405 can be performed with the centrifuge spinning at high speed. Alternatively, for fixed sample volumes, with ordinary zonal operation (not continuous-flow), the pili sample does not flow continuously into the centrifuge 405 for long periods of loading, but rather the entire sample volume, which must be less than the annular volume of the centrifuge, is loaded into the centrifuge. The rotor volume is then closed off before acceleration to high speed. After loading and centrifuging to achieve banding, the pili containing bands are recovered by displacing the bands sequentially, with lowest density bands exiting first and highest density last. As the density of each pili uniquely determines the position of that pili or particle in the exiting stream, the timing of the detection of specific pili particles provides particle density information.

In operation, pili sample liquid is introduced into the density gradient within the centrifuge rotor at the low-density end of the gradient, and each particle or molecule penetrates into the gradient at a rate that increases with the mass of the particle, and with the density. In the case of a protein molecule, the mass is much smaller than that of a pili by at least an order of magnitude, and the density is about the same as that of a relatively low-density virus. Accordingly, the rate of banding for proteins is much slower than for viruses. The proteins will then primarily be to the low-density side of their equilibrium positions, as they started on that side. Since the equilibrium position of most proteins in a gradient is nominally about 1.3 g/ml, at the operating time, most proteins are positioned considerably lower than 1.3. Once the pili are banded, the centrifuge is decelerated to low speed, and the gradient is recovered by pumping dense fluid of preferably 60% CsCl from the gradient supply system to the centrifuge. The dense fluid displaces the gradient, with low density bands exiting first followed by high density bands. The procedure is complete in a few minutes, and the cycle repeats again beginning with the loading of the density gradient at low speed. Ultracentrifugation provides the advantages of universal capture of all catalogued and non-cataloged pili, with high capture efficiencies and a high degree of pili separation from the background components.

The pili filtrate from the second purifying and concentrating stage 401 is then fed to a detecting stage 501. A detailed description of the detection stage 501 of the present invention including the gas-phase electrophoretic mobility molecular analyzers (GEMMA), the electrospray assembly (ES), the differential mobility analyzer (DMA), and the condensation particle counter (CPC) assembly is provided in co-pending U.S. Pat. No. 7,250,138 and related U.S. Pat. Nos. 6,051,189, 6,485,686, and 6,491,872, all of which are incorporated by reference herein in their entireties.

EXAMPLE

This test example analyzes the direct counting of "hairlike" pili structures as shown in FIGS. 1 and 2 for specific gram positive bacteria. These structures are also found on many other classes of bacteria and lead to the interesting possibility of determining a direct method for analysis by counting their numbers and determining a concentration. Indications show that these structures are intact after removal from the bacteria cell and are sufficiently different from species to species of bacteria to give an indication of bacteria type if not actual identification of the bacteria [St. Geme III, et al, 1996; Fader, et al, 1982, See References cited]. The pili removed from the bacteria were analyzed using the physical nanometer counting methodology in the Integrated Virus Detection System (IVDS) and Electrospray ionization-mass spectrometry.

As indicated above, bacteria are completely different types of microorganisms than viruses. They are a magnitude larger in size than viruses. Bacteria are classified in their own scheme. They have cell walls, are organized into cellular components and generally are considered to be among the self-sustaining organisms. In this sense, viruses are sometimes not even considered to be alive and have a completely different life cycle than that of the viruses. These physical and physiological differences between bacteria and viruses render the development of a universal detector capable of their simultaneous detection and characterization.

Additionally, Electrospray Ionization-Mass Spectrometer (ESI-MS) has been reported as an effective technique capable of providing accurate identification of various microorganisms based on their proteomic or genomic contents [Yates III, 1998; Thomas, et al, 1998; Krishnamurthy, et al, 2000]. Also, the pili of the bacteria are made up mainly of protein molecules, which makes ESI-MS a suitable technique to interrogate these structures and provide a complimentary information to that that is obtained from their analysis using IVDS technique.

IVDS can differentiate particles from 5-950 nm in size. Bacteria are generally 0.5-1 micron wide and 2-3 microns long, well outside the physical ability of IVDS. There are, however, interesting features on the surface of a bacterium that are in the proper size range for IVDS to characterize. The bacteria surface is more complex than that of the surfaces of ordinary cells. Gram-negative bacteria, named because of their inability to retain crystal violet-iodine complex stain, have rigid surface appendages called "pili".

These "hair-like" structures are around 7 nm in diameter and vary in length, up to 25 nm for the longer flagellate [Eisenberg. 1999], which are other nanometer-sized structures that can be attached to the surface of bacteria. The pili are composed of structural protein sub-units called "pilins." Some structures have only one structural protein unit, while other pili are more complex and have several. These pili consist of a precise helical arrangement of one or more types of protein and as indicated may have different lengths for different bacteria. Choudhury [Choudhury, et al, 1999] and others discuss crystal complexes associated with pilin subunits. Cell lysis breaks the cell into components. Lysis can be achieved by changes in pH, temperature, and ultrasonication treatment or by addition of chemical reagents. The pili can then been treated as any nanometer particle, separated and counted. Different pili proteins for different bacteria species can be expected. Evidence in this manner suggests that IVDS is capable of interrogating these virus-sized bacteria components and in this manner detect bacteria.

Recent advances in the field of proteomics, where it is desirable to obtain a comprehensive mapping of the expressed proteins in an organism, provide a promising strategy to characterize bacteria using their protein biomarkers [Fleischmann, et al, 1995; Bussey, et al, 1995; Yates III, 1998; Thomas, et al, 1998; Krishnamurthy, et al, 2000]. Mass spectrometry (MS) is widely used in proteomic field for the characterization of various microorganisms by either identifying as many protein components as possible biomarkers [Yates III, 1998] or identifying one or several protein component(s) in a complex mixture [Thomas, et al, 1998; Krishnamurthy, et al, 2001. Various MS techniques have been more extensively used to characterize bacteria than viruses [Thomas, et. al., 1998; Krishnamurthy, et al, 2000; Dai, et al, 1999]. Many factors attributed to this phenomenon, such as the significant number of protein biomarkers encoded in bacteria, and thermal stability bacterial proteins upon introduction into the ionization source of the MS [Tong, et al, 1999; Karty, et al, 1998; Bothner, et al, 1999; Valegard, et al, 1990].

MS had been also used to study the filamentous protein structures, which are found in the pili part of bacterial cells [Tito, et al, 2000; Thomas, et. al., 1998; Cargile, et al, 2001]. Most studies were oriented toward the investigation of the post-translation modification of the pili proteins that play important role in disease carrying from various microorganisms, mainly Neiseseria meningitides [Stimson, et al, 1996]. However, attempts to investigate the pili proteins in *Bacillus subtilis* using MS or IVDS has not reported in the literature. These studies address the characterization of the pili proteins of *Bacillus subtilis* samples that were processed using various sample processing conditions and approaches. Using MS is a complimentary technique to IVDS where accurate and discriminatory characteristics and properties of the biomolecules are revealed.

Experimental Procedures IVDS

Figure 11:
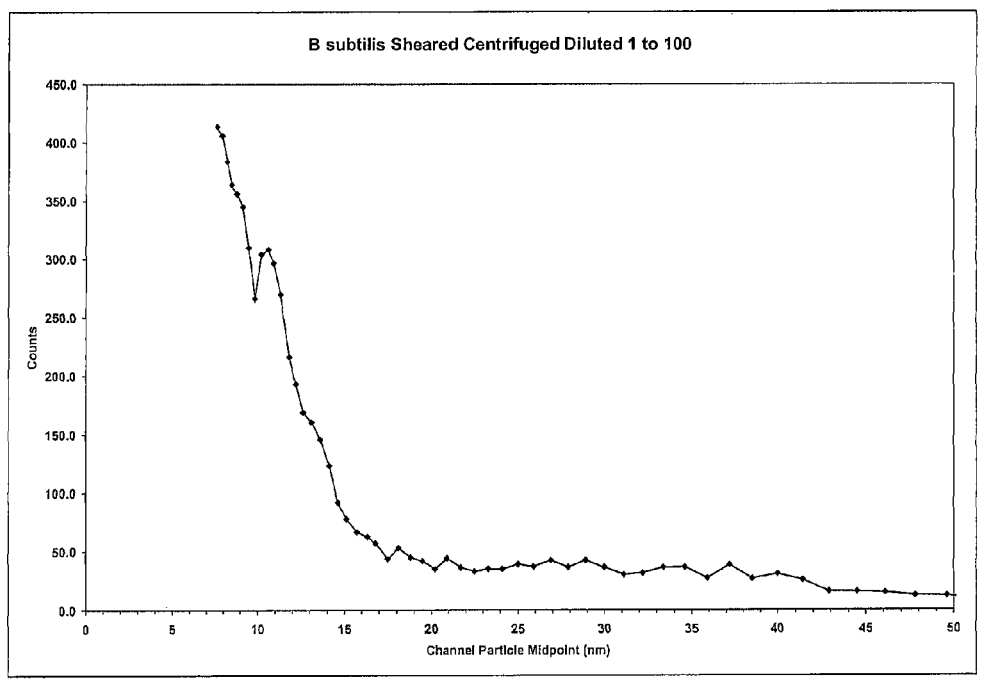
FIG. 11 is a graph of bacterial pili sheared from B. subtillis (3 scan average, BS2)

A strain of *Bacillus subtilis* ATCC 15561 was prepared according to manufacture protocol, www.atcc.org. Briefly, *Bacillus subtilis* samples were produced by growing the bacteria on nutrient agar plates at 30° C. for 26 hrs. The bacterial cells were collected by scraping them into distilled water and pelleting them by centrifugation at 12,000 g for 10 minutes. The bacterial samples were washed four times in distilled water by centrifugation. The bacterial sample was re-suspended in distilled water. A 0.5 ml aliquot of the stock solution was passed in and out of a 22 ga. needle to break the pili from the surface of the bacteria. The shearing action of repeated passages through the needle has been shown to remove pili from bacteria [Baron, et al, 2001]. The sample was centrifuged at 12,000 rpm (10,000 g) for 25 minutes to pelletize the large bacterial cells. The supernatant was collected and diluted 1 to 100 with 20 mlvi ammonium acetate for examination in the IVDS (designated B52). FIG. 11 shows the peak associated with the bacterial pili between 10 and 12 nm.

Figure 12:
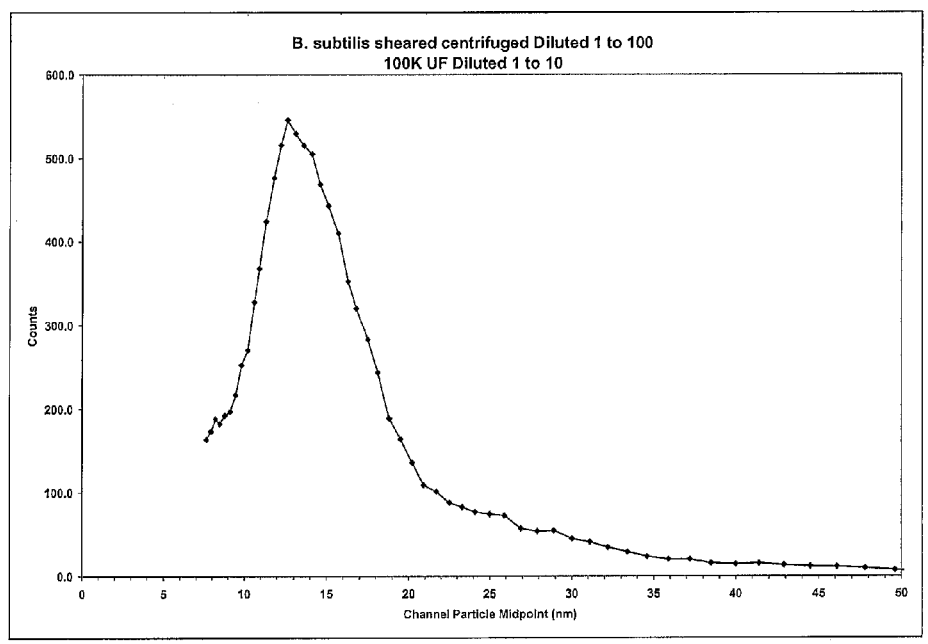
FIG. 12 is a graph of bacterial pili unfiltered (5 scan average, BS3)

The sample B52 was filtered by the Ultra Filtration (UF) subsystem of the IVDS using 100K Dalton filter (for details on the IVDS and its different sub-systems the reader is referred to a companion report [Wick et al, 2004]). The purpose of the filtration system is to remove any material with molecular weight smaller than the filtration system is set for (100K Daltons in this case), such as growth media, salt molecules, and proteins from the solution [Wick and McCubbin, 1999] and leave a concentrated pili solution. The filtered sample was diluted 1 to 10 with 20 mM ammonium acetate before analysis with the IVDS. FIG. 12 shows the ultrafiltered bacterial sample with the peak at 12 nm (designated BS3).

Figure 13:
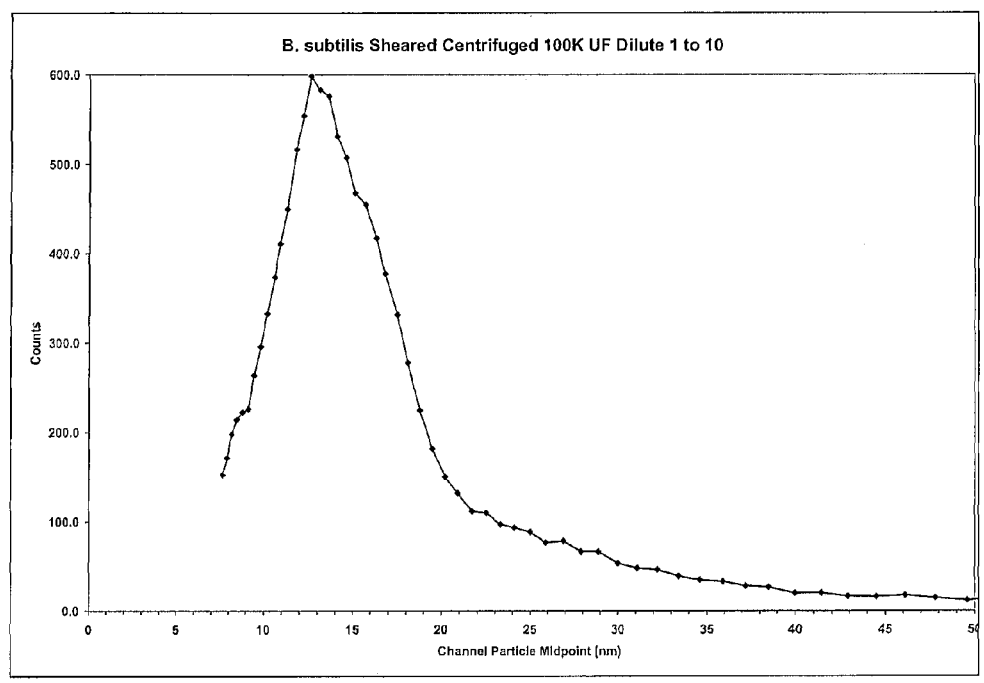
FIG. 13 is a graph of bacterial pili ultrafiltered from neat sample (6 scan average, BS1)

The original sheared sample was also ultrafiltered, before dilution, using a 100K Dalton filter and analyzed with the IVDS. After filtration, the filtered sample was diluted 1 to 10 with 20 ml via ammonium acetate before analysis with the IVDS. FIG. 13 shows the ultrafiltered neat bacterial sample with the peak at 12 nm (designated BS1).

Mass Spectrometry

ESI-MS Parameters

An ion trap mass spectrometer (LCQ-Deca, Thermo Finnigan-USA) equipped with an ESI ion source was used. The mass spectrometer was operated under the control of the XCaliber program with a manual deconvolution algorithm. Spectra were collected in the positive ion mode. Three microscans were used with a maximum ion injection time of 200 ms. The ESI spray voltage was maintained at 4 kV. The capillary voltage was maintained at 23 V, and the temperature of the ion transport tube was 190° C. The mass spectrometer was calibrated to achieve a ±2 Da resolution using a mixture of cytochrome c, BSA, insulin, and myoglobin proteins.

Automated Deconvolution Algorithm Analysis

The automated in-house deconvolution algorithm was developed to provide a filtered mass list instead of a conventional peak-at-every-mass output for the BSPS-MS analysis of bacterial extracts. A detailed procedure for the automated in-house software will be presented elsewhere. Briefly, the in-house software deconvolutes the bacterial protein masses through analysis of a raw mass spectral file. Mass range, isotope peak width, S/N threshold, and maximum number of returned peaks user input parameters were selected prior to the start of the deconvolution process. The software identified LC peaks and deconvoluted their corresponding average mass spectra to generate a list of masses. The total deconvolution process takes 10 minutes for a 60-minute BSPS-ESI-MS analysis time. The deconvolution process is interfaced with relational database management software to update the in-house database with experimental bacterial protein masses.

Results and Discussions

IVDS

The sample of *B. subtilis* that was sheared and shown in FIG. 11 displays the pili protein at 12 nm next to a very large peak, less than 10 nm, that results from cellular and growth media contamination. The large contamination peak was removed by ultrafiltration of the sample. The ultrafiltration molecular weight cut-off (MWCO) was 100K Daltons that allowed the removal of growth media and salts while retaining the pili fragments. After ultrafiltration, the peak showing the pili in solution was more pronounced and not masked by other contaminants. To determine if the 1 to 100 dilution, before ultrafiltration and IVDS analysis, affected the pili, the neat sample was ultrafiltered after shearing and centrifuging. As shown in FIG. 13, the results from IVDS does not show any significant difference from the diluted and ultrafiltered sample, shown in FIG. 12.

Mass Spectrometry

Mass Spectrometry Results

The unsurpassed sensitivity of ESI-MS analysis to biomolecules is an ideal technique to utilize in order to determine the molecular weight of intact proteins and their identity. The expansion and extensive genomic and proteomic databases provide relevant information for the identity of the biomolecules present in the analyzed sample in this study. Application of Liquid Chromatography-Mass Spectrometry (LC-MS) to the characterization of biomolecules originated from various parts of bacterial cells has been successful in numerous studies [Yates III, 1998; Thomas, et al, 1998; Krishnamurthy, et al, 2000; Dai, et al, 1999; Jensen, et al, 1999]. In this study, the *Bacillus subtilis* samples underwent different sample processing approaches. Some *Bacillus subtilis* samples were sheared, and centrifuged without any further filtration, these samples were labeled as BS 1. The other *Bacillus subtilis* samples were exposed to similar sample processing but followed by centrifugation, dilution, and finally molecular weight cut-off using 100K Dalton membrane to remove cellular debris and large particulates, these samples were labeled as BS2 and BS3.

Figure 14:
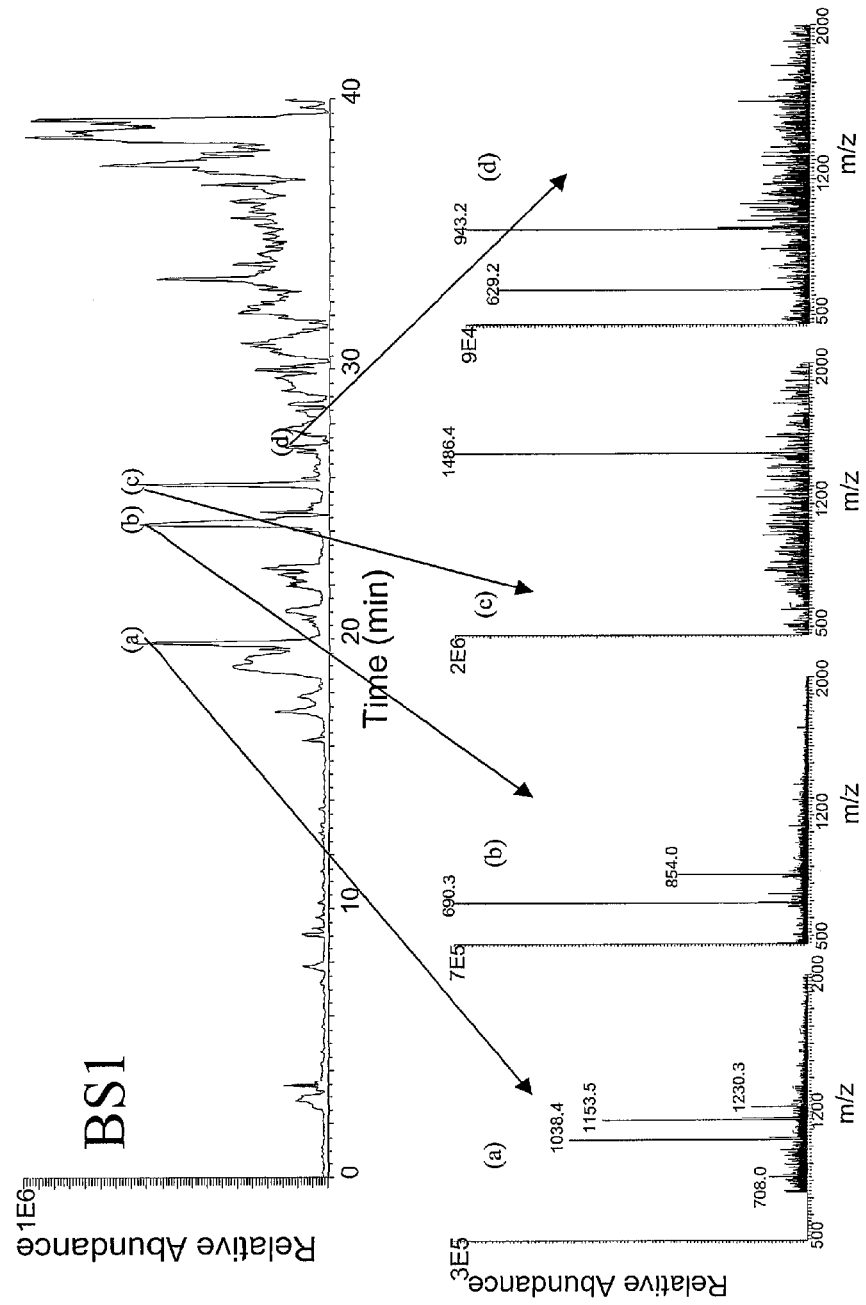
FIG. 14 is a graph of *Bacillus subtilis* sample (BS1) sheared without further filtration. The upper graph represents the total ion chromatogram of its LC-MS analysis. The lower graphs are the mass spectra of the dominant peaks observed in replicate runs, N=3.

FIG. 14 shows the LC-MS analysis result of the BS 1 sample. The upper chromatogram represents the total ion chromatogram of BS 1 and the lower spectra are the mass spectra of the dominant proteins detected in this sample by the ion trap mass spectrometer. It was observed that the peaks appeared toward the end of the TIC were the result of the presence of large amount of buffer in the sample, this is reflected in the non-symmetrical peak shape, which is characteristic of a mixture of non-proteinaceous molecules. Upon examining the mass list generated from the LC-MS analysis of BS 1 the above mass spectra represents protein characteristic of the pili and flagella parts of the bacterial cell.

Comparison of the experimentally deconvoluted protein molecular weights with those that are presented in the public database, Swissprot*, resulted in matching the former proteins with the outer coat and the extracellular proteins that are associated with pili and flagella parts of the bacterial cell [Lei, et al, 1998]. The molecular mass lists of the bacterial proteins are shown in Table 2. This table also enlists the accession numbers that correspond with the identified protein obtained from the LC-MS analysis of BS 1.

Figure 15:
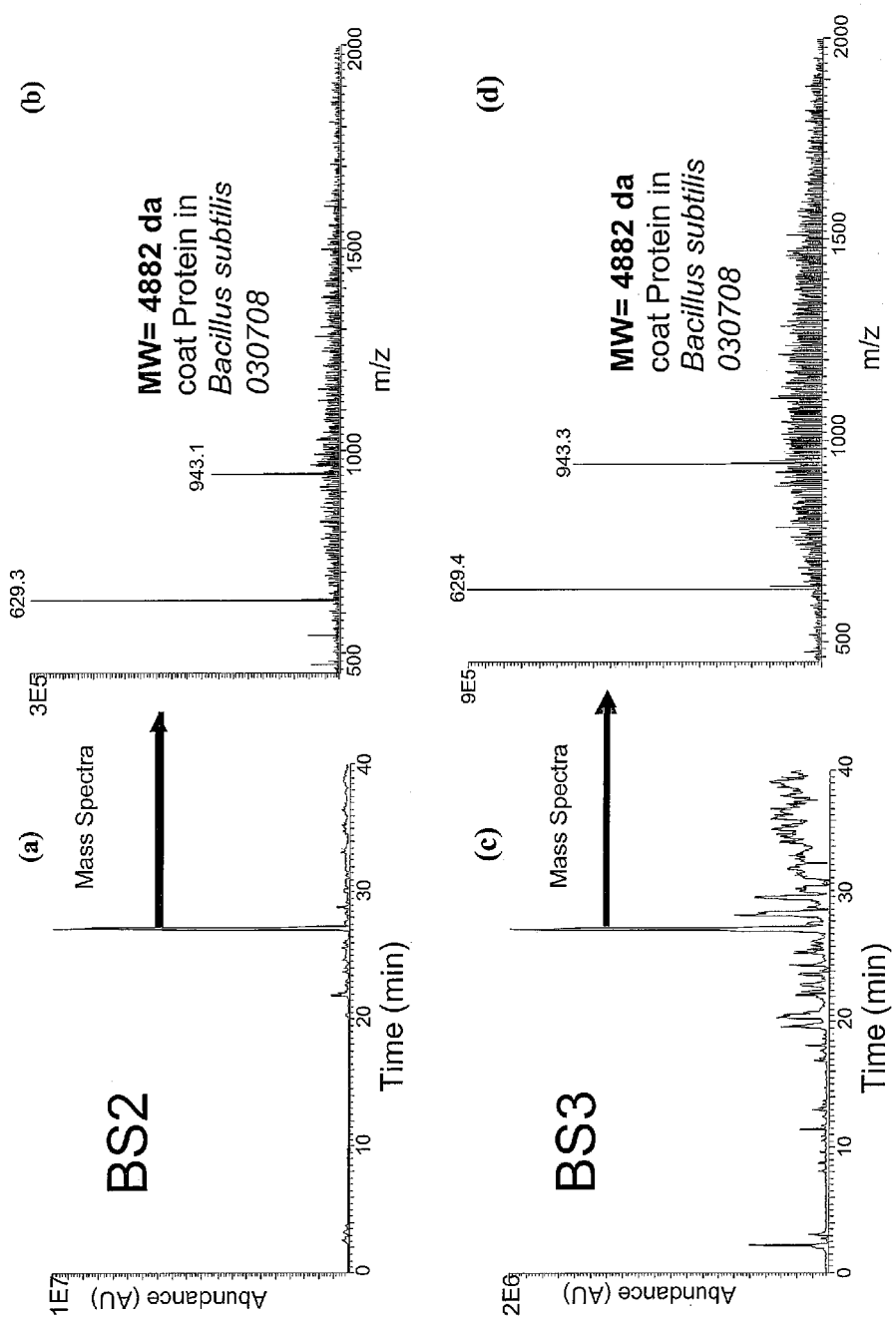
FIG. 15 is a graph of the effect of concentration on the reproducibility of the LC-MS analysis of Pili extracts of *Bacillus subtilis*. (a) Total ion Chromatogram of *bacillus subtilis* sample (BS2) sheared, centrifuged, and filtered using 100 Kda ultrafiltration membrane. (b) Mass spectrum of the most intense peak from the TIC of BS2. (c) Total ion Chromatogram of *bacillus subtilis* sample (BS3) sheared, centrifuged, and filtered using 100 Kda ultrafiltration membrane and 100 fold dilution than that of BS2. (d) Mass spectrum of the most intense peak from the TIC of BS3.

The LC-MS analyses of the sheared and filtered *Bacillus subtilis*, BS2 and BS3, samples showed significant resemblance between their TIC plots and the dominant bacterial proteins identified. It is interesting to note that the TIC plots (a) and (b) in FIG. 15 are characterized by a dominant peak that has same retention time observed in the LC-MS analyses of these bacterial extracts. This dominant peak is an indication of significant expression of this protein compared to the other observed proteins. The mass spectra of this dominant peak revealed that the same protein was found in both samples with better S/N observed in BS2 than that with BS3. The difference in S/N ratio for that mentioned protein could be due to the fact that BS3 was diluted 100 fold than that of BS2. The identity of the peak revealed that it is a coat protein in *Bacillus subtilis*, which is an indication of the effectiveness of the sample processing approach in isolating the desired parts of the bacterial cells, in this case the pili. It is also worth mentioning that this coat protein was observed in BS1 sample but with lower peak intensity that those observed in the TIC plots of BS2 and BS3 samples.

Figure 16:
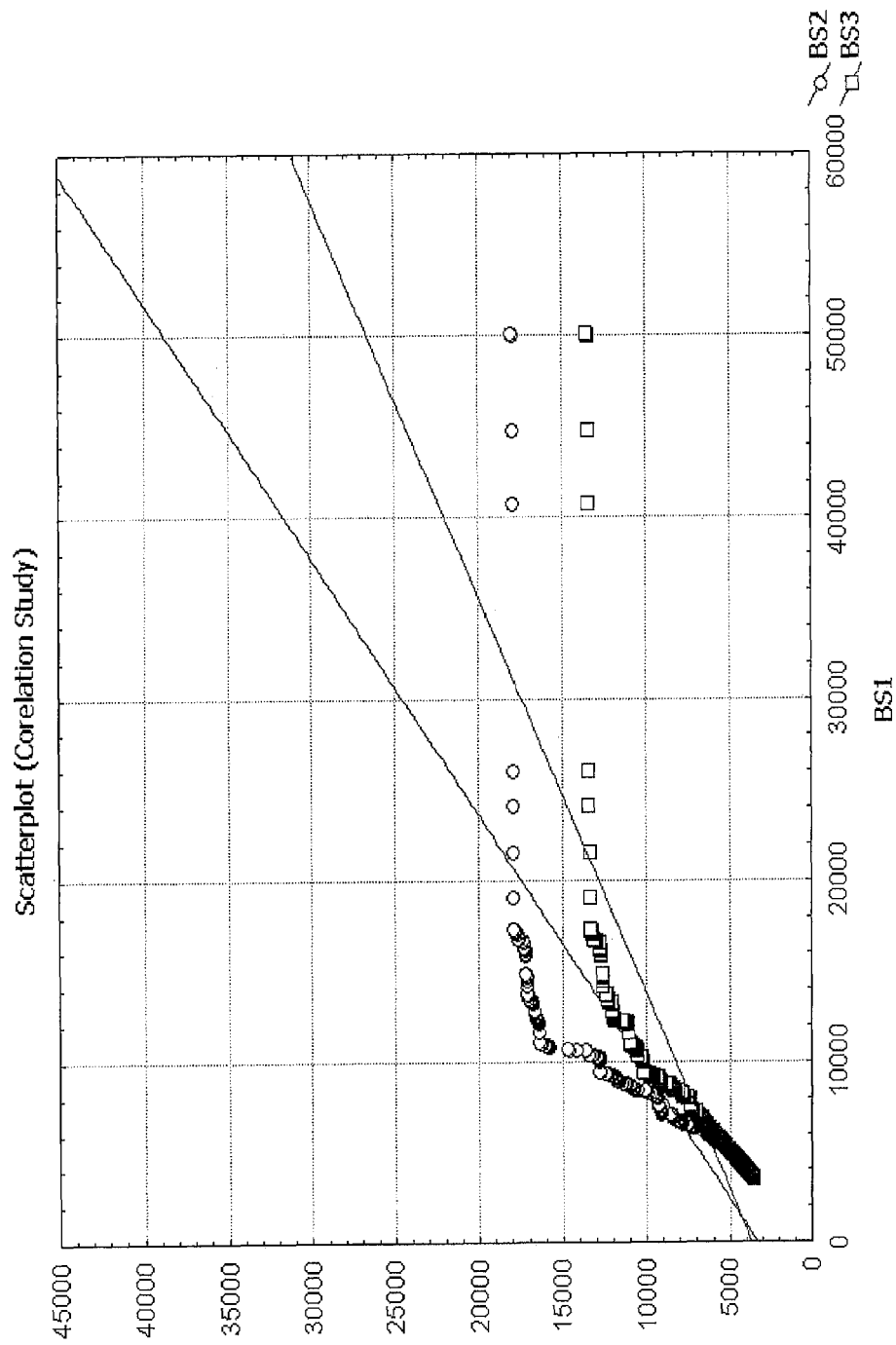
FIG. 16 is a graph of the molecular weight correlation of BS1 vs. BS2 & BS3. Only BS2 and BS3 were exposed to ultrafiltration with molecular weight cut-off of 100 Kda membrane; and, FIG. 17 is a graph of the molecular weight correlation between the protein masses generated from *Bacillus subtilis* samples, BS2 and BS3. Both samples underwent similar sample processing procedures with the latter diluted by 100× than the former sample.
Figure 17:
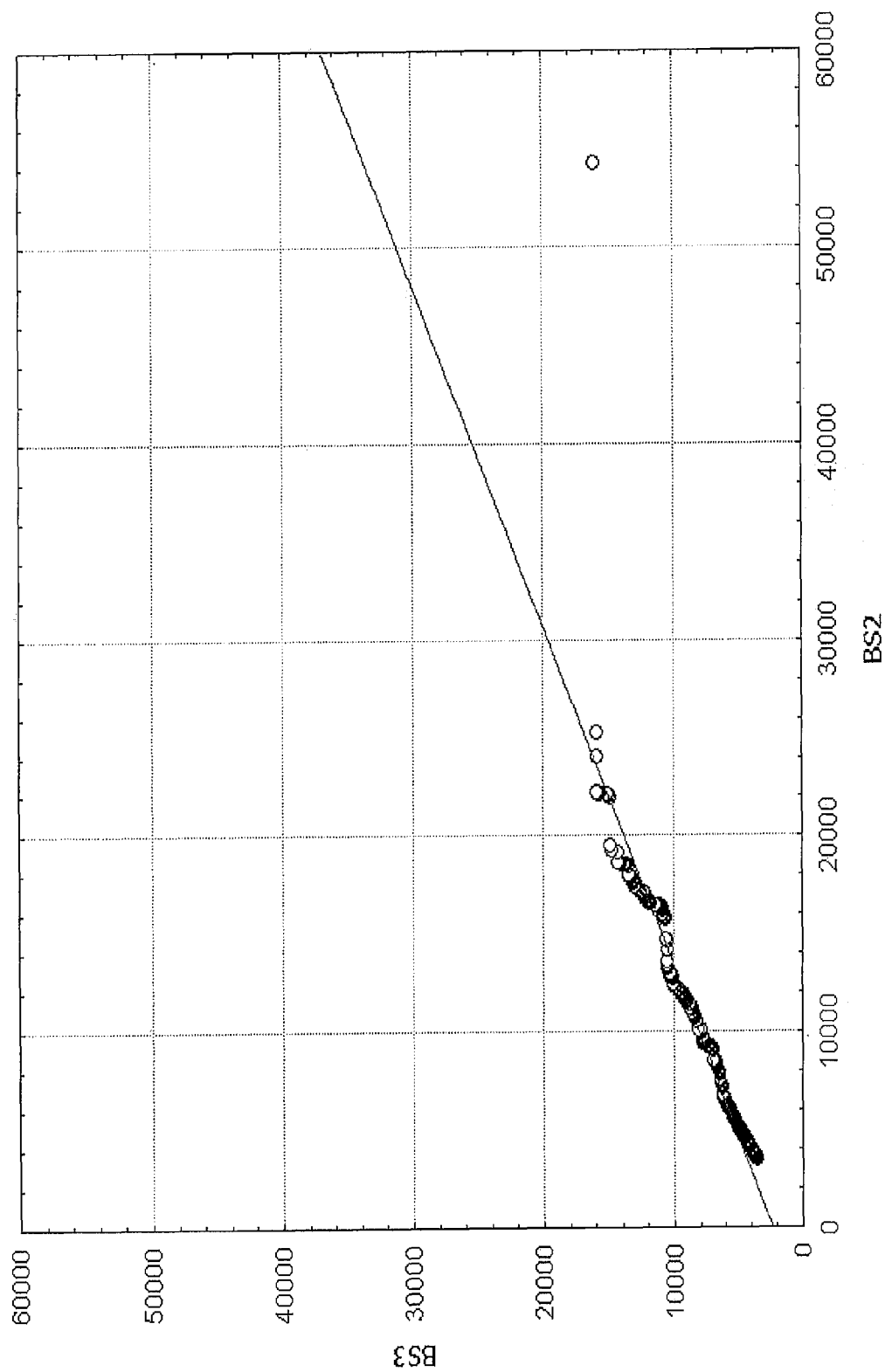

The LC-MS data were further investigated to determine the data reproducibility and the effect of sample processing on the LC-MS analyses of *Bacillus subtilis* extracts. FIG. 16 shows the reproducibility of the molecular weight of the experimentally deconvoluted proteins generated from the LC-MS analyses of the *Bacillus subtilis* extract samples. The masses generated for these samples were then averaged from three replicate LC-MS analyses per each sample. The statistical correlation study showed a higher number of common masses were observed between BS2 and BS3 than that with BS1. FIG. 16 also reflects the relevance of comparing the mass lists generated from differently processed bacterial extract samples because as the correlation factor among samples increase it indicates a resemblance in the sample processing approach as evident in this case. Sample BS2 and BS3 were processed under similar conditions with only difference in the dilution as compared to BS1. Additionally, this observation was supported upon comparison of the deconvoluted mass lists generated for BS2 and BS3 where over 99% of the masses were matching with each other as shown in FIG. 17.

Comparison of the correlation in the masses among all samples is presented in Table 3, where the correlation factor of 99% match is observed between BS2 and BS3, as compared with 80-81% match with BS1. Overall, the LC-MS provided a confirmatory technique on the data obtained from the IVDS analysis. The similarity between the IVDS and LC-MS analysis of the *Bacillus subtilis* samples is observed. The similarity in comparing the IVDS data among the *Bacillus subtilis* extract samples was also observed within their corresponding LC-MS analyses.

CONCLUSIONS

The IVDS system is well suited for rapid physical measurements of the submicron pili of bacteria after mechanical removal. The pili were shown to be from *Bacillus subtilis* through mass spectrometry analysis. The collected LC-MS data of the bacterial samples showed that most detected proteins belonged to the pili region in the cell. The ability of LC-MS to decipher the identity of the bacterial proteins and track their position in the bacterial cell qualify the LC-MS technique to be a complimentary and confirmatory technique to the IVDS, which identify the bacterial pili based on their size and concentration. Due to differences between the LC-MS technique as compared to that of IVDS, the pili samples may require further sample preparation prior to its analysis by LC-MS as evident in the presence of interference peaks in some of the reported MS spectra, see FIG. 14.

It may be possible, with further experimentation, to correlate the rapid identification of bacterial groups with the straightforward counting methodology of the IVDS and their proteomic identification capability using the LC-MS technique.

TABLE 2

|     | MW data | Description | Accession Number |
| --- | --- | --- | --- |
| (a) | 13545 | Transmembrane Protein | O-05219 |
| (b) | 4096 | Extracellular Protein | Q-9R623 |
| (c) | 14880 | Outer Coat Protein | P-54520 |
| (d) | 4882 | Outer Coat Protein | O-30708 |

Table 2. Dominant protein masses from *Bacillus subtilis* sample # 1 (BS1) deconvoluted using in-house algorithm with their corresponding descriptions and accession numbers from their matching with a public database (Swissprot).

TABLE 3

|     | BS1 | BS2 | BS3 |
| --- | --- | --- | --- |
| BS1 | 1.00 | 0.80 | 0.81 |
| BS2 | 0.80 | 1.00 | 0.99 |
| BS3 | 0.81 | 0.99 | 1.00 |

Table 3. Statistical correlation of the LC-MS analyses of *Bacillus subtilis* samples that underwent different sample preparation approaches; marked correlations are significant at p<(less than) 0.05000.

REFERENCES

1. Baron, Christian, et al, "Elevated Temperature Differentially Affects Virulence, VirB Protein Accumulation, and T-Pilus Formation in Different *Agrobacterium tumefaciens* and *Agrobacterium vitis* Strains", Journal of Bacteriology, December 2001, pgs. 6852-6861.
2. Bothner, B.; Schneemann, A.; Marshall, D.; Reddy, V.; Johnson, J. E.; Siuzdak, G., "Crystallographically identical virus capsids display different properties in solution", Nat. Struct. Biol. 1999, 6, 114-116.
3. Bussey, H.; Storms, R. K.; Ahmed, A.; Albermann, K,; Allen, K.; Ansorage, W.; Araujo, R.; Aparicio, A.; Barrell, B.; Badcock, K.; et al., "Histone Hi in *Saccharomyces cerevisiae*", Science 1995, 269, 496-512.

4. Cargile, B. J., Mcluckey, S. A., J. L. Stephenson, "Identification of Bacteriophage MS2 Coat Protein from *E. coli* Lysates via Ion Trap Collisional Activation of Intact Protein Ions", Anal. Chem. 2001, 73, 1277-1285.

5. Choudhury, et. al. "X-ray structure of the FimC-FimH chaperone-adhesion complex from uropathogenic *Escherichia coli*", Science, 7 Aug. 99, 285:1061.

6. Dai, Y.; Li, L.; Roser, D. C.; Long, S. R., "Detection and identification of low-mass peptides and proteins from solvent suspensions of *Escherichia coli* by high performance liquid chromatography fractionation and matrix-assisted laser desorption/ionization mass spectrometry". Rapid Commun. Mass Spectrom. 1999, 13, 73-78.

7. Eisenberg, David, "How chaperones protect virgin proteins", Science 13 Aug. 99, 85: 1021.

8. Fader, Robert C., et al, "Purification and Chemical Characterization of Type 1 Pili Isolated from *Klebsiella pneumoniae*", The Journal of Biological Chemistry Vol. 257, No. 6, March 25, pp. 3301-3305, 1982

9. Fleischmann, R.; Adams, M.; White, 0.; Clayton, R.; Kirkness, E.; Kerlavage, A.; Bult, C.;. Tomb, J.; Dougherty, B.; Merrick, J.; "Whole-genome random sequencing and assembly of *Haemophilus Influenza* Rd", et al. Science 1995, 269, 496-5 12.

10. Jensen, P. K.; Pasa-Tolic, L.; Anderson, G. A.; Homer, J. A.; Lipton, M. S.; Bruce. J. E.; Smith, R. D., "Probing Proteomes Using Capillary Isoelectric Focusing Electrospray Ionization Fourier Transform Ion Cyclotron Resonance Mass Spectrometry", Anal. Chem. 1999, 71, 2076-2084.

11. Karty, J. A.; Lato, S.; Reilly, J. P., "Detection of the bacteriological sex factor in *E. coli* by matrix-assisted laser desorption/ionization time-of-flight mass spectrometry", J. Rapid Commun. Mass Spectrom. 1998, 12, 625-629.

12. Krishnamurthy, T.; Rajamani, U.; Ross, P. L.; Jabbour, R.; Nair, H.; Eng, J.; Yates, J.; Davis, M. T.; Stahl, D. C.; Lee, T. D. J. Toxicol.-Toxin Rev. 2000, 19, 95-117.

13. Lei, Q. P., Cui, X., Kurtz D. M. J., Amster, I. J., Chemushevich, I. V., Standing, K. G., "Electrospray mass spectrometry studies of non-heme iron-containing proteins", Anal chem., 70, 1998, 1838-1846.

14. St. Geme III, Joseph W., et al. "*Haemophilus influenzae* Pili are composite structures assembled via the Hiffi chaperone", Proc. Natl. Acad. Sci. USA Vol. 93, pp. 11913-11918, October 1996.

15. Stimson, Elaine, et al., "Discovery of a novel protein modification: alphaglycerophosphate is substituent of meningococcal Pilin", Biochem, J., 315, 1996, 29-33.

16. Thomas, J. J.; Falk, B.; Fenselau, C.; Jackman, J.; Ezzell, J., "Viral characterization by direct analysis of capsid proteins", Anal. Chem. 1998, 70, 3863-867.

17. Tito, Mark A., Kasper T., Karmn V., Janos H., Robinson C., "Electrospray Time-of-Flight Mass Spectrometry of the Intact M52 Virus Capsid", JACS, 2000, 122, 3550-3551.

18. Tong, W.; Link, A.; Eng, J. K.; Yates, J. R., "Identification of Proteins in Complexes by Solid-Phase Microextraction/Multistep Elutionl Capillary Electrophoresis/Tandem Mass Spectrometry", Anal. Chem. 1999, 71, 2270-2278.

19. Valegard, K.; Liljas, L.; Fridborg, K.; Unge, T., "The three-dimensional structure of the bacterial virus MS2", Nature 1990, 345, 36-41.

20. Wick, Charles H., McCubbin, Patrick E., and Birenzvige, Amnon, "Detection and Identification of Viruses Using the Integrated Virus Detection System (IVDS)" an ECBC technical report, in print December 2004.

21. Wick, C. H., McCubbin, P. E., "Purification of MS2 bacteriophage from complex growth media and resulting analysis by the integrated virus detection system (IVDS)", Toxicology Methods 9:253-263, 1999

22. Yates, J. R., III., "Mass spectrometry and the age of the protcome", J. Mass Spectrom. 1998, 33, 1-19.

What is claimed is:

1. An apparatus for detecting and identifying bacteria in a sample taken from the environment, comprising:
    (a) a collecting means for collecting a sample from the environment;
    (b) a means for purifying and concentrating the bacteria in said sample, said purifying and concentrating means connected to said collecting means;
    (c) a means for separating pili from the purified and concentrated bacteria in said sample, said separating means connected to said means for purifying and concentrating the bacteria;
    (d) a means for purifying and concentrating the separated pili in the sample based on size, said means for purifying and concentrating the separated pili connected to said means for separating pili from the bacteria; and
    (e) means for detecting the purified and concentrated pili and thereby detecting said bacteria, wherein the detecting means comprises: an electrospray assembly which receives the output from the purifying and concentrating means for placing a charge on the purified and concentrated pili under the influence of an electric field, a differential mobility analyzer which receives the output from the electrospray assembly for separating the charged pili according to size, and a condensation particle device for counting the number of sized pili received from the differential mobility analyzer, said detecting means connected to said means for purifying and concentrating the separated pili.

2. The apparatus of claim 1, wherein the means for purifying and concentrating the separated pili comprises an ultracentrifuge for density-gradient ultracentrifugation of the sample so that the pili are banded according to density.

3. The apparatus of claim 1, wherein the collecting means comprises a collector having means for liquid scrubbing a collected fluid sample of aerosol and gaseous materials containing the bacteria and a means for reducing the size of solid materials in the fluid sample.

4. The apparatus of claim 1, wherein the collecting means comprises a liquid sample collector.

5. The apparatus of claim 1, wherein the collecting means collects samples of airborne aggregates which contain the bacteria and wherein the aggregates have sizes in the range of about 2-10 microns.

6. The apparatus of claim 1, further comprising a first conduit means connected to the collecting means and the means for purifying and concentrating the bacteria for conveying the sample from the collecting means to the means for purifying and concentrating the bacteria.

7. The apparatus of claim 1, wherein said means for separating pili from bacteria in said sample comprises one or more means selected from the group consisting of chemical means, heating means, and physical or mechanical means.

8. The apparatus of claim 7, wherein said means for separating pill from bacteria comprises a housing having a plunger contained therein, wherein liquid sample containing bacteria is forced by said plunger through an outlet in said housing having an adjustable restriction.

9. The apparatus of claim 8, further comprising means for heating said housing and introducing pH adjusting chemicals into said sample contained in said housing.

10. The apparatus of claim 6, further comprising a second conduit means connected to the means for purifying and concentrating the bacteria and the means for separating pili from the bacteria, a third conduit means for connecting the means for separating the pili from bacteria to the means for purifying and concentrating the pili, and fourth conduit means connecting the means for purifying and concentrating the pili to the means for detecting the purified and concentrated pili.

11. The apparatus of claim 1, wherein the means for purifying and concentrating the pill is selected from the group consisting of a filter apparatus and a centrifuge.

12. An apparatus for detecting the presence of bacteria in a sample taken from the environment, comprising:
(a) a collecting means for collecting a sample from the environment;
(b) a means for separating pili from bacteria in said sample, said separating means connected to said collecting means;
(c) a means for purifying or concentrating the separated pili connected to said separating means, for separating the pili based on the size of the pili; and
(d) detecting means for detecting the separated pili connected to the means for purifying and concentrating the separated pili, said detecting means comprising: an electrospray assembly for receiving the separated pili and for placing a charge on the separated pili, a differential mobility analyzer which receives the output from the electrospray assembly for separating the charged pill based on the size of the charged pili, and a condensation particle device for counting the number of separated charged pili received from the differential mobility analyzer.

13. The apparatus of claim 12, wherein said means for purifying and concentrating the separated pili is selected from the group consisting of filter means and centrifuge means.

14. The apparatus of claim 12, wherein said means for separating pili from bacteria in said sample is selected from the group consisting of chemical means, heat means, physical or mechanical means, and combinations thereof.

15. An apparatus for detecting the presence of bacteria in a sample taken from the environment, comprising:
(a) a collecting means for collecting a sample containing bacteria from the environment;
(b) a separating means for separating pili from bacteria in said sample, said separating means connected to said collecting means;
(c) a second separating means for separating the pili in the collected sample based on size;
(d) means for detecting the separated pili, wherein the detecting means comprises: an electrospray assembly for receiving the separated pili and for placing a charge on the separated pili introduced into the electrospray assembly, a differential mobility analyzer which receives the output from the electrospray assembly for separating the charged pili according to the size of the charged pili, and a condensation particle device for counting the number of separated pili received from the differential mobility analyzer; and
(e) valve means connected to the collecting means, the separating means, and the detecting means, the valve means including a means for selectively feeding the collected sample containing the pili either to the separating means or the detecting means.

16. The apparatus of claim 15, wherein the collecting means comprises an ultracentifuge wherein the bacteria are banded according to density by density-gradient ultracentrifugation.

* * * * *